US008367417B2

(12) United States Patent
Stevenson et al.

(10) Patent No.: US 8,367,417 B2
(45) Date of Patent: Feb. 5, 2013

(54) METHODS FOR DETERMINING DYSREGULATION OF METHYLATION OF BRAIN EXPRESSED GENES ON THE X CHROMOSOME TO DIAGNOSE AUTISM SPECTRUM DISORDERS

(75) Inventors: Roger E. Stevenson, Greenwood, SC (US); Julie R. Jones, Greenville, SC (US); Cindy D. Skinner, Greenwood, SC (US); Michael J. Friez, Cross Hill, SC (US)

(73) Assignee: Greenwood Genetic Center, Inc., Greenwood, SC (US)

( * ) Notice: Subject to any disclaimer, the term of this patent is extended or adjusted under 35 U.S.C. 154(b) by 0 days.

(21) Appl. No.: 13/170,795

(22) Filed: Jun. 28, 2011

(65) Prior Publication Data

US 2011/0269132 A1 Nov. 3, 2011

Related U.S. Application Data

(62) Division of application No. 12/510,316, filed on Jul. 28, 2009, now Pat. No. 7,998,744.

(60) Provisional application No. 61/084,063, filed on Jul. 28, 2008.

(51) Int. Cl.
C12Q 1/68 (2006.01)
(52) U.S. Cl. .............................. 436/94; 436/91; 435/6.11
(58) Field of Classification Search .................... 436/86, 436/94, 91, 501, 503, 63; 435/4, 6, 7.1, 7.4; 600/300; 506/16, 17, 18
See application file for complete search history.

(56) References Cited

FOREIGN PATENT DOCUMENTS

WO WO 2005/024064 A2 3/2005

OTHER PUBLICATIONS

Jamain, Stephane et al. "Mutations of the X-linked genes encoding neuroligins NLGN3 and NLGN4 are associated with autism." Nature Genetics (2003) 34 27-29.*
Simonati, A. et al. "A novel missense mutation in the L1CAM gene in a boy with L1 disease." Neutrol. Sci. (2006) 27 114-117.*
Abrahams et al., "Advances in autism genetics: on the threshold of a new neurobiology," *Nature Reviews/Genetics*, vol. 9, May 2008, pp. 341-355.
Albert Schinzel, "Microdeletion syndromes, balanced translocations, and gene mapping," *Journal of Medical Genetics*, vol. 25, 1988, pp. 454-462.
Allen et al., "Methylation of *Hp*aII and *Hh*aI Sites Near the Polymorphic CAG Repeat in the Human Androgen-Receptor Gene Correlates with X Chromosome Inactivation," *Am. J. Hum. Genet.*, vol. 51, 1992, pp. 1229-1239.
American Psychiatiric Association: Diagnostic and Statistical Manual of Mental Disorders, Fourth Edition, Text Revision. American Psychiatric Association, Washington, DC, 2000.
Article—Folstein et al., "Genetics of Autism: Complex Aetiology for a Heterogeneous Disorder," *Nature Reviews/Genetics*, Vol, 2, Dec. 2001, pp. 943-955.
Article—H. A. Lubs, "A Marker X Chromosome," *Am. J. Hum. Genet.*, vol. 21, 1969, pp. 231-344.
Article—Marshall et al., "Structural Variation of Chromosomes in Autism Spectrum Disorder," *The American Journal of Human Genetics*, vol. 82, Feb. 2008, pp. 477-488.
Article—Nicholls et al., "Genetic imprinting suggested by maternal heterodisomy in non-deletion Prader-Willi syndrome," *Nature*, vol. 342, Nov. 16, 1989, pp. 281-285.
Bailey et al., "Autism as a strongly genetic disorder: evidence from a British twin study," *Psychological Medicine*, vol. 25; 1995, pp. 63-77.
C. Sue Carter, "Sex differences in oxytocin and vasopressin: Implications for autism spectrum disorders?," *Behavioural Brain Research 176*, 2007, pp. 170-186.
C.M. Freitag, "The genetics of autistic disorders and its clinical relevance: a review of the literature," *Molecular Psychiatry*, vol. 12, 2007, pp. 2-22.
Campbell et al., "A genetic variant that disrupts *MET* transcription is associated with autism," *PNAS*, vol. 103, No. 45, Nov. 7, 2006, pp. 16834-16839.
Chen et al., "Establishment and Maintenance of DNA Methylation Patters in Mammals," *CTMI*, vol. 301, 2006, pp. 179-201.
Chiurazzi, et al., "XLMR genes: updated 2007", *European Journal of Human Genetics*, 16, pp. 422-434, (2008).
Craig, et al., "Application of microarrays to the analysis of the inactivation status of human X-linked genes expressed in lymphocytes", *European Journal of Human Genetics*, 12, pp. 639-646, (2004).
David H. Skuse, "Imprinting, the X-chromosome, and the Male Brain: Explaining Sex Differences in the Liability of Autism," *Pediatric Research*, vol. 47, No. 1, Jan. 2000, 13 pages.
Engel et al., "Uniparental Disomy, Isodisomy, and Imprinting: Probable Effects in Man and Strategies for Their Detection," *American Journal of Medical Genetics*, vol. 40, 1991, pp. 432-439.
Evans, Julie C., et al., "Early onset seizures and Rett-like features associated with mutations in CDKL5", *European Journal of Human Genetics* (2005), 13, 1113-1120.
Forstein, et al., Infantile autism: a genetic study of 21 twin pairs. J. Child Psychol. Psychiatry 18:297, 1977.
Friez et al., "Recurrent Infections, Hypotonia, and Mental Retardation Caused by Duplication of *MECP2* and Adjacent Region in Xq28," *Pediatrics*, vol. 118, No. 6, Dec. 2006, pp. e1687-e1695.
Grant R. Sutherland, "Fragile Sites on Human Chromosomes: Demonstration of Their Dependence on the Type of Tissue Culture Medium," *Science*, vol. 197, 1977, pp. 265-266.
Hu, et al., "Gene expression profiling of lymphoblastoid cell lines from monozygotic twins discordant in severity of autism reveals differential regulation of neurologically relevant genes", *BMC Genomics*, 7:118, (2006).

(Continued)

*Primary Examiner* — Yelena G Gakh
*Assistant Examiner* — Christopher A Hixson
(74) *Attorney, Agent, or Firm* — Dority & Manning, P.A.

(57) ABSTRACT

The discovery that alterations in methylation, which can cause one or more genes on the single X chromosome in males to be partially silenced or overexpressed, constitute a predisposition to autism spectrum disorders is generally disclosed herein. These alterations provide the rationale and basis for methods to diagnose autism spectrum disorders.

12 Claims, 7 Drawing Sheets

OTHER PUBLICATIONS

Irizarry, et al., "Comprehensive high-throughput arrays for relative methylation (CHARM)", *Genome Research*, 18:780-790, (2008).

James et al., "Metabolic Endophenotype and Related Genotypes are Associated with Oxidative Stress in Children with Autism," *American Journal of Medical Genetics Part B (Neuropsychiatric Genetics)*, vol. 141B, 2006, pp. 947-956.

James, et al., "Abnormal Trasmethylation/transsulfuration Metabolism and DNA Hypomethylation Among Parents of Children with Autism", *J Autism Dev Disord*, 38:1966-1975, (2008).

James, et al., "Metabolic biomarkers of increased oxidative stress and impaired methylation capacity in children with autism", *Am J Clin Nutr*, 80:1611-1617, (2004).

Jiang et al., "A Mixed Epigenetic/Genetic Model for Oligogenic Inheritance of Autism with a Limited Role for UBE3A," *American Journal of Medical Genetics*, vol. 131A, 2004, pp. 1-10.

John P. Hussman, "Suppressed Gabaergic Inhibition as a Common Factor in Suspected Etiologies of Autism," *Journal of Autism and Developmental Disorders*, vol. 31, No. 2, 2001, pp, 247-248.

Jones, et al., "Hypothesis: Dysregulation of Methylation of Brain-Expressed Genes on the X Chromosome and Autism Spectrum Disorders", *American Journal of Medical Genetics Part A*, 146A:2213-2220, (2008).

Kleefstra, T., et al., "Zinc finger 81 (ZNF81) mutations associated with X-linked mental retardation", Journal of Medical Genetics (2004) 41, 394-399.

Livak et al., "Analysis of Relative Gene Expression Data Using Real-Time Quantitative PCR and the $2^{-\Delta\Delta C}T$ Method, "*Methods*, vol. 25, 2001, pp. 402-408.

Lubs at al., "XLMR Syndrome Characterized by Multiple Respiratory Infections, Hypertelorism, Severe CNS Deterioration and Early Death Localizes to Distal Xq28," *American Journal of Medical Genetics*, vol. 85, 1999, pp. 243-248.

M. E. Grant, "DNA methylation and mental retardation," *Clin. Genet.*, vol. 73, 2008, pp. 531-534.

Martin et al., "Analysis of Linkage Disequilibrium in -Aminobutyric Acid Receptor Subunit Genes in Autistic Disorder.," *American Journal of Medical Genetics (Neuropsychiatric Genetics)*, vol. 96, 2000, pp. 43-48.

Mary F. Lyon, "Gene Action in the X-chromosome of the Mouse (*Mus musculus* L.)," *Nature*, vol. 190, Apr. 22, 1961, pp. 372-373.

Meinkoth et al., "Hybridization of Nucleic Acids Immobilized on Solid Supports," *Analytical Biochemistry*, vol. 138, 1984, pp. 267-284.

McClean, Phillip, "DNA-Basics of Structure and Analysis", Dec. 8, 2010, 1998.

Meins at al., "Submicroscopic duplication in Xq28 causes increased expression of the *MECP2* gene in a boy with severe mental retardation and features of Rett syndrome," *J. Med. Genet.*, vol. 42, 2005, 6 pages.

Miles et al., "Development and Validation of a Measure of Dysmorphology: Useful for Autism Subgroup Classification," *American Journal of Medical Genetics Part A*, vol. 145A, 2008, pp. 1101-1116.

Mill, et al., "Epigenomic Profiling Reveals DNA-Methylation Changes Associated with Major Psychosis", *The American Journal of Human Genetics*, 82, 696-711, Mar. 2008.

Morrow et al., "Identifying Autism Loci and Genes by Tracing Recent Shared Ancestry," *Science*, vol. 321, Jul. 11, 2008, pp. 218-223.

Morrow, et al., "Identifying Autism Loci and Genes by Tracing Recent Shared Ancestry", *Science*, vol. 321, Jul. 11, 2008.

N. Carolyn Schanen, "Epigenetics of autism spectrum disorders," *Human Molecular Genetics*, vol. 15, Review Issue No. 2, 2006, pp. R138-R150.

Nagarajan, et al., "Reduced MeCP2 expression is frequent in autism frontal cortex and correlates with aberrant MECP2 promoter methylation", *Epigenetics*, 1(4):e1-11, (2006).

Nelson et al., "Neuropeptides and Neurotrophins in Neonatal Blood of Children with Autism or Mental Retardation," *Ann. Neurol.*, vol. 49, 2001, pp. 597-606.

Nishimura, et al., "Genome-wide expression profiling of lymphoblastoid cell lines distinguishes different forms of autism and reveals shared pathways", *Human Molecular Genetics*, vol. 16, No. 14, pp. 1682-1698, (2007).

Oberléet al., "Instability of a 550-Base Pair DNA Segments and Abnormal Methylation in Fragile X Syndrome," *Research Article*, May 25, 1991, pp. 1097-1102.

Pai et al., "A new X linked recessive syndrome of mental retardation and mild dysmorphism maps to Xq28," *J. Med. Genet.*, vol. 34, 1997, pp. 529-534.

Purcell, A.E., et al., "Postmortem brain abnormalities of the glutamate neurotransmitter system in autism", *Neurology* (2001), 57, 1618-1628.

Qiao Y, et al., "Autism-associated familial microdeletion of Xp11.22", *Clin Genet*, 74:134-144, (2008).

Ritvo et al., "Evidence for Autosomal Recessive Inheritance in 46 Families with Multiple Incidences of Autism," *Am. J. Psychiatry*, vol. 142, No. 2, Feb. 1985, pp. 187-192.

Samuels, Benjamin Adam, et al., "Cdk5 Promotes Synaptogenesis by Regulating the Subcellular Distribution of the MAGUK Family Member CASK", *Neuron* 2007, 56, 823-837.

Schendel et al., "Birth Weight and Gestational Age Characteristics of Children with Autism, Including a Comparison with Other Developmental Disabilities," *Pediatrics*, vol. 121, No. 6, Jun. 2008, pp. 1155-1165.

Schroer et al, "Autism and Maternally Derived Aberrations of Chromosome 15q." *American Journal of Medical Genetics*. vol. 76, 1998, pp. 327-336.

Sebat et al., Strong Association of De Novo Copy Number Mutations with Autism, *Science*, vol. 316, Apr. 20, 2007, pp. 445-449.

Shimabukuro, et al., "Global hypomethylation of peripheral leukocyte DNA in male patients with schizophrenia: A potential link between epigenetics and schizophrenia", *Journal of Psychiatric Research*, 41, pp. 1042-1046, (2007).

Steffenburg et al., "A Twin Study of Autism in Denmark, Finland, Iceland, Norway and Sweden," *J. Child Psychol.*, vol. 30, No. 3, 1989, pp. 405-416.

Stevenson, et al., X-Linked Mental Retardation. Oxford Univ. Press, New York, 2000.

Thomas et al., "Xp deletions associated with autism in three females," *Hum. Genet.*, vol. 104, 1999, pp. 43-48.

Ullmann et al., "Array CGH Identifies Reciprocal 16p13.1 Duplications and Deletions That Predispose to Autism and/or Mental Retardation," *Human Mutation*, vol. 28, No, 7, 2007, pp. 674-682.

Van Esch et al., "Duplication of the *MECP2* Region Is a Frequent Cause of Severe Mental Retardation and Progressive Neurological Symptoms in Males," *Am. J. Hum. Genet.*, vol. 77, 2005, pp. 442-453.

Weiss et al., "Association between Microdeletion and Microduplication at 16p11.2 and Autism," *The New England Journal of Medicine*, vol. 358, No. 7, Feb. 14, 2008, pp. 667-675.

Wilson et al., "Epigenomics—Mapping the Methylome," *Cell Cycle*, vol. 5, No. 2, Jan. 16, 2006, pp. 155-158.

Yu et al., "Fragile X Genotype Characterized by an Unstable Region of DNA," *Science*, vol. 252, May 24, 1991, pp. 1179-1181.

\* cited by examiner

METHODS FOR DETERMINING DYSREGULATION OF METHYLATION OF BRAIN EXPRESSED GENES ON THE X CHROMOSOME TO DIAGNOSE AUTISM SPECTRUM DISORDERS

CROSS REFERENCE TO RELATED APPLICATIONS

The present application claims filing benefit to and is a divisional application of U.S. patent application Ser. No. 12/510,316 filed on Jul. 28, 2009 of Stevenson, et al., and claims filing benefit of U.S. provisional patent application having the Ser. No. 61/084,063 filed on Jul. 28, 2008 entitled "Methods for Determining Dysregulation of Methylation of Brain Expressed Genes on the X Chromosome to Diagnose Autism Spectrum Disorders," Roger E. Stevenson, Julie R. Jones, Cindy D. Skinner, and Michael J. Friez, inventors, both of which are incorporated by reference herein in their entirety.

BACKGROUND

Autism spectrum disorders include a group of serious and enigmatic neurobehavioral disorders that usually become apparent early in childhood and persist as lifelong disabilities. Disturbances in three categories of behavior (reciprocal social interactions, verbal and nonverbal communications, and age appropriate activities and interests) are considered hallmarks of autism.

The number of children diagnosed with autism has greatly increased in recent decades. At the midpoint of the 20th Century, autism was narrowly defined and uncommonly diagnosed (with a prevalence of about four per 10,000). Greater awareness, availability of services, changes in diagnostic criteria to include a broader spectrum of neurodevelopmental abnormalities, and possibly other factors have contributed to the ten-fold or greater increase in the frequency with which autism spectrum disorder is diagnosed (current prevalence of 40-60 per 10,000). One extraordinary aspect of the epidemiology is the three-fold to six-fold excess of males.

Autism appears causally heterogeneous. Although scientists have long abandoned the idea that autism is caused by humorless and rigid parenting, they have been unable to identify specific cause(s) in any substantial proportion of cases. Standardized criteria for autism (DSM IV-TR) may be assessed based on parental, caregiver, and/or examiner observations using the Autism Diagnostic Interview, Revised (ADI-R) and Autism Diagnostic Observation Schedule (ADOS). A small percentage of patients will have coexisting genetic disorders and an even smaller percentage a history of an environmental insult.

Only meager evidence exists to suggest that environmental insults play a significant role in the causation of autism. Prenatal and postnatal infections (rubella, cytomegalovirus, herpes) have been documented in a few cases. Little evidence exists to suggest injury in the perinatal period as a causative factor, although low birth weight and premature birth has been noted as a risk factor (Schendel et al. 2008). Although autism has been reported among infants with prenatal exposure to thalidomide, cocaine, alcohol, and valproate, most infants prenatally exposed to these and other drugs or chemical agents do not develop autism. Considerable attention has been given to the concept that immunizations for measles, mumps, and rubella (MMR) might cause autism. However, repeated study has not provided evidence to support this theory.

No laboratory finding is consistently abnormal, although plasma serotonin levels may be elevated in affected individuals and first-degree relatives. In a promising study, Nelson et al. (2001) found several neuropeptides and neurotrophins (vasoactive intestinal peptide, calcitonin gene-related peptide, brain-derived neurotrophic factor and neurotrophin 4/5) to be elevated in newborn blood spots from infants who were later found to have autism. Confirmation of these findings has not been reported by other investigators. More recently, James et al. (2006, 2008) have proposed that metabolic vulnerability to oxidative stress may be an autism susceptibility factor, and Carter (2007) has suggested that the skewed male:female ratio in autism may be explained by sex-specific responses to the neuropeptides, oxytocin and vasopressin.

The genetic contribution to the causation/predisposition to autism is considered to be substantial on the basis of high concordance in monozygous twins, a recurrence rate of about 5% among siblings, the uniquely high male:female ratio (about 4:1 in most studies), the co-occurrence of autism with a number of single gene disorders and chromosome aberrations, and the presence of behavioral disturbances among first degree relatives. These considerations aside, no specific genetic cause has been found to explain more than 1-2% of autism cases, and overall only in 10-20% of autism cases can a cause be determined.

The strongest evidence for a heritable basis of autism comes from twin studies. Overall, these studies show high concordance of autism among monozygous (MZ) twins and low concordance among same sex dizygous (DZ) twins, resulting in greater than ninety percent heritability estimates. Four prominent studies dealing specifically with autistic disorder (narrowly defined to exclude Asperger disorder and pervasive developmental disorder) report concordance of 36-96% in MZ twins and 0-30% in same-sex DZ twins (Folstein and Rutter 1977, Ritvo et al. 1985, Steffenburg et al. 1989, Bailey et al. 1995).

Chromosomal abnormalities have been found in a number of individuals with autism. These include marker chromosomes, microdeletions and microduplications, rearrangements, and autosomal fragile sites (Schroer et al. 1998, Ullmann et al. 2007, Morrow et al. 2008, Freitag 2007, Sebat et al. 2007, Weiss et al. 2008, Marshall et al. 2008). Taken together, these observations do not suggest a single underlying chromosomal aberration, but rather that a variety of chromosomal changes may disturb brain development and function in a way that leads to autism. Chromosome aberrations observed in more than one case of autism include: 1q deletion, 15q deletion or duplication, 16p deletion or duplication, 17p deletion, 18q deletion, 22q deletion, and Xq28 deletion or duplication.

Several single gene entities have been found in association with autism. Most notably are the fragile X syndrome, Rett syndrome, tuberous sclerosis, phenylketonuria, Angelman syndrome, and adenylosuccinate lyase deficiency. Mutations in the neuroligins, neurexins, GABA receptors, reelin, ENGRAILED 2, SLC6A4 serotonin transporter, glutamate receptor 6, DHCR7, DLX5, MET, RPL10, SHANK3, CNTNAP2, BDNF, and other genes have been associated with autism and are properly considered candidate autism susceptibility genes (Schanen 2006, Freitag 2007, Abrahams and Geschwind 2008).

A number of genome-wide screens to identify chromosomal regions linked to autism susceptibility have been reported. The linkage evidence appears greatest for one or two loci on chromosome 7q, and loci on chromosomes 1q, 2q, 3p, 3q, 5p, 6q, 9q, 11p, 15q, 16p, 17q, and 19p. The study of candidate genes within the linkage regions has failed to identify genes that clearly cause or strongly predispose to autism.

Although several X-linked genes (NLGN3, NLGN4, RPL10, FMR1, MECP2 and ten others noted with an asterisk in the Table and FIG. 1) have been associated with autism or autistic features in males, X-chromosomal loci have not been implicated in autism by linkage analyses. This may be explained in part by existence of multiple X loci of importance (heterogeneity) or by the uninformative nature of the sib-pairs used in the analysis. Of greater importance is that linkage analysis would not detect epigenetic modifications of gene(s) on the X chromosome.

The recurrence rate in brothers and sisters of affected persons is 3-8%. This recurrence rate is less than expected if all cases were caused by autosomal recessive gene mutations (25%) or autosomal dominant gene mutations (50%). The rate is not unlike that found in conditions considered to have multifactorial causation, such as neural tube defects and cleft lip/palate. Multifactorial causation implies a collaboration between multiple genetic factors and environmental influences.

Soon after the discovery of the correct number of chromosomes in humans, the importance of gene dosage to human development and health was appreciated. Inactivation of an X chromosome in normal females, as reflected in formation of the sex chromatin body, was recognized and considered to equalize (at 1N) the dosage of X-linked genes between females and males (Lyon 1961). Trisomies, which augmented the gene dosage (to 3N) for genes on individual chromosomes, were found to be uniformly associated with mental defect and malformation, in most cases lethal before birth. Deletions of small segments of the genome, which reduced gene dosage segmentally to 1N, were likewise found to be associated with malformations and mental retardation—e.g., Cri du Chat, Miller-Dieker, Smith Magenis, velocardiofacial, Wolff-Hirschhorn, and other microdeletion syndromes (Schinzel 1988, Pai et al. 2002). These findings and others reinforce the concept that diallelic expression of autosomal genes and monoallelic expression for genes on the sex chromosomes are the norm for humans.

In the 1980s and 1990s, evidence was found, initially in mice and then in humans, that diallelic expression was not the norm for all autosomal gene loci (Nicholls et al. 1989, Engel and DeLozier-Blanchet 1991). Rather, expression of certain genes, found in specific clusters on several autosomes, was noted to be monoallelic, while the second allele, although present, was silenced. Further, the expressed gene was consistently derived from the same parent and the silenced gene from the other. Such parent specific influence on gene activity was designated imprinting.

Appreciation for the role of imprinted genes in the causation of human disease has grown steadily since these initial findings. Currently, at least twelve human chromosomes (1, 4, 6, 7, 8, 10, 11, 14, 15, 18, 19, and 20) are known to harbor gene loci that are imprinted. Genome-wide, however, less than 1% of autosomal genes appear to be imprinted, and hence have monoallelic and parent specific expression.

Several lines of evidence link imprinted regions and autism predisposition. Schanen (2006) has pointed out that the gene loci with suggestive or possible linkage to autism overlap or are in close proximity to regions subject to genomic imprinting. The evidence is strongest for loci on 7q and 15q. Duplication of proximal 15q, when derived from the mother, has been associated with autism. When duplication from the same region is derived from the father, autism does not occur. Deletions of the maternal copy of the same region on 15q, paternal disomy, and mutations of UBE3A cause Angelman syndrome, a disorder that typically presents with autistic features and mental retardation. Hence, silencing or overexpression of genes from this region appears to predispose to autism. Jiang et al. (2004) have proposed a mixed epigenetic and genetic model for autism based on abnormal DNA methylation at the 5' CpG island of UBE3A, on chromosome 15, in one autism brain, decreased E6-AP protein (product of UBE3A) in several autism brains, and sharing of paternal 15q alleles in one cohort of autism sibpairs. MECP2, the X chromosomal gene responsible for Rett syndrome, exerts its effect by binding individual CpGs and recruiting other repression-related factors. A primary target of this effect is UBE3A, the gene responsible for Angelman syndrome. This may explain the clinical similarities between Rett and Angelman syndrome. Hussman (2001) and Martin et al. (2000) have suggested that GABAergic inhibition predisposes to autism. Three GABA receptor subunits (GABA $\alpha$, $\beta$, $\gamma$) are located near the imprinted region of chromosome 15q.

Less work has been performed on the putative autism loci on 7q. Campbell et al. (2006) have found the C allele in the promotor of MET receptor tyrosine kinase in the 7q31 autism candidate region to be a risk factor in autism. The C allele reduces MET expression and alters binding of transcription factors. Schanen (2006) reviewed the status of genes in the imprinted cluster on 7q21.3 finding several attractive candidates, but none that had conclusive evidence for autism susceptibility. Freitag (2007) suggested that RELN, LAMB1, and EN2 were perhaps the three most promising autism candidate genes on chromosome 7.

Skuse (2000) has proposed that at least one loci on the X chromosome is imprinted, being expressed only from the paternal chromosome. Patients with Turner syndrome (45,X) who have a maternal X are more vulnerable to impairments in language and social interactions, whereas those with a paternal X may be protected, having significantly better social adjustment and superior language skills. Xp deletions of the boundary between the Xp pseudoautosomal region and marker DXS7103 have been found in three females with autism (Thomas et al. 1999).

Silencing and overexpression of genes with normal DNA sequence on the single X chromosome in males and the active X chromosome in females have been identified as biological phenomena of significance. The most prominent example of gene silencing occurs in the fragile X syndrome. The pathology is based on expansion and methylation of a CGG repeat in the 5' untranslated region of the FMR1 gene. Methylation and silencing of expression typically occur when the CGG repeat number exceeds 200 copies (Lubs 1969, Sutherland 1977, Oberle et al. 1991, Yu et al. 1991). Overexpression of MECP2 caused by duplication of the gene and adjacent region in Xq28 has been documented in numerous cases of males with mental retardation, hypotonia, and recurrent infections (Pai et al. 1997, Lubs et al. 1999, Van Esch et al. 2005, Friez et al. 2006). Males with duplication of MECP2 likewise have an increased risk of autism spectrum disorders (Meins et al. 2005, Friez et al. 2006).

The various chromosomal alterations and gene mutations currently reported in association with autism indicate the genetically heterogeneous nature of autism and taken together account for only a minority (less than 20%) of cases.

SUMMARY

Objects and advantages of the invention will be set forth in part in the following description, or may be obvious from the description, or may be learned through practice of the invention.

According to one embodiment, a method for determining predisposition to or diagnosis of autism spectrum disorder in an individual is generally disclosed. For example, the method can include determining a cytosine methylation level of at least three different test polynucleotide sequences. Each test polynucleotide sequence comprises at least one gene on the X chromosome, and each test polynucleotide sequence is obtained from the individual.

The method also includes comparing the cytosine methylation level of each test polynucleotide sequence to a control cytosine methylation range of a corresponding control polynucleotide sequence. The control cytosine methylation range of the corresponding control polynucleotide sequence can be developed from data obtained from a control group comprising non-affected age matched individuals. A finding that the cytosine methylation level of at least about 20% of the test polynucleotide sequences falls outside of the control cytosine methylation range of the corresponding control polynucleotide sequences leads to a determination that the individual is predisposed to or affected with autism spectrum disorder.

In one preferred embodiment, the cytosine methylation level comprises cytosines at CpG dinucleotide sites.

The three or more different test polynucleotide sequences to be tested can include any genes of the X-chromosome and, optionally, can also include flanking sequences to the genes. For instance, in one embodiment, all of the genes of the X-chromosome can be tested. In other embodiments, smaller sets of genes can be tested. For example, the genes of the three or more test polynucleotide sequences can include all XLMR genes; the 85 XLMR genes of Table 1 (discussed further herein); a set of genes including NLGN4, NLGN3, L1CAM, and AVPR2; a set of genes including NLGN4, STK9, ARX, NLGN3, AGTR2, FMR1, RPL10, SLC6A8, MECP2, ARHGEF6, FACL4, MED12, JARID1C, TM4SF2, AP1S2; and so forth.

According to another embodiment, a method for determining predisposition to or diagnosis of autism spectrum disorder in an individual that includes determining the presence or quantity of at least three different biomarkers in a test sample obtained from the individual is generally disclosed. Each of the at least three different biomarkers are specific for a different test X-chromosome gene. The method also includes determining an expression level of each of the test X-chromosome genes based upon the presence or quantity in the test sample of the biomarker for that test X-chromosome gene, and comparing the expression level of each of the test X-chromosome genes to a corresponding control expression level. A finding that at least about 20% of the test X-chromosome genes are either overexpressed or underexpressed to a significant degree from the corresponding control expression level corresponds to a determination that the individual is predisposed to or affected with autism spectrum disorder.

By way of example, the test X-chromosome genes can include the 44 genes of Table 2 (described further herein); genes found at chromosomal locations Xp11.2 to Xp11.4, Xp21 to Xp22, Xq23 to Xq24 or Xq25; the group of genes including CLCN4, WWC3, AMOT, KIAA2022, CDKL5, DMD, GPR64, SCML1, FHL1, and MAP7D2; the group of genes including CLCN4, WDR44, NGLN3, CDKL5, KIAA2022, AMOT, MAP7D2, and TBC1D8B; the group of genes including CASK, CFP, CDKL5, LONRF3, RNF12, MID1, RP2, SCML1, ZNF81, ELK1, and PQBP1; and so forth.

Biomarkers can be any suitable material for determining the expression level of the genes including mRNA, proteins, and the like.

Also disclosed herein are arrays suitable for use in determining the expression levels of biomarkers for determining predisposition for or diagnosing an individual affected with ASD. For example, the array can include a plurality of probes, where each probe being specific for a biomarker (e.g., mRNA, protein, etc.) of an X-chromosome gene.

Other features and aspects of the present invention are discussed in greater detail below.

BRIEF DESCRIPTION OF THE FIGURES

A full and enabling disclosure of the present disclosure, including the best mode thereof to one skilled in the art, is set forth more particularly in the remainder of the specification, which includes reference to the accompanying figures, in which:

FIG. 8 represents scatterplots of the degree of expression of selected genes on the X chromosome that are generally underexpressed in males with autism (solid triangles) as compared to unaffected males (open circles). The two genes with encircled triangles on the scatterplots have 8 or more autism samples with expression values below the range of values for unaffected males.

DEFINITIONS

Figure 1:
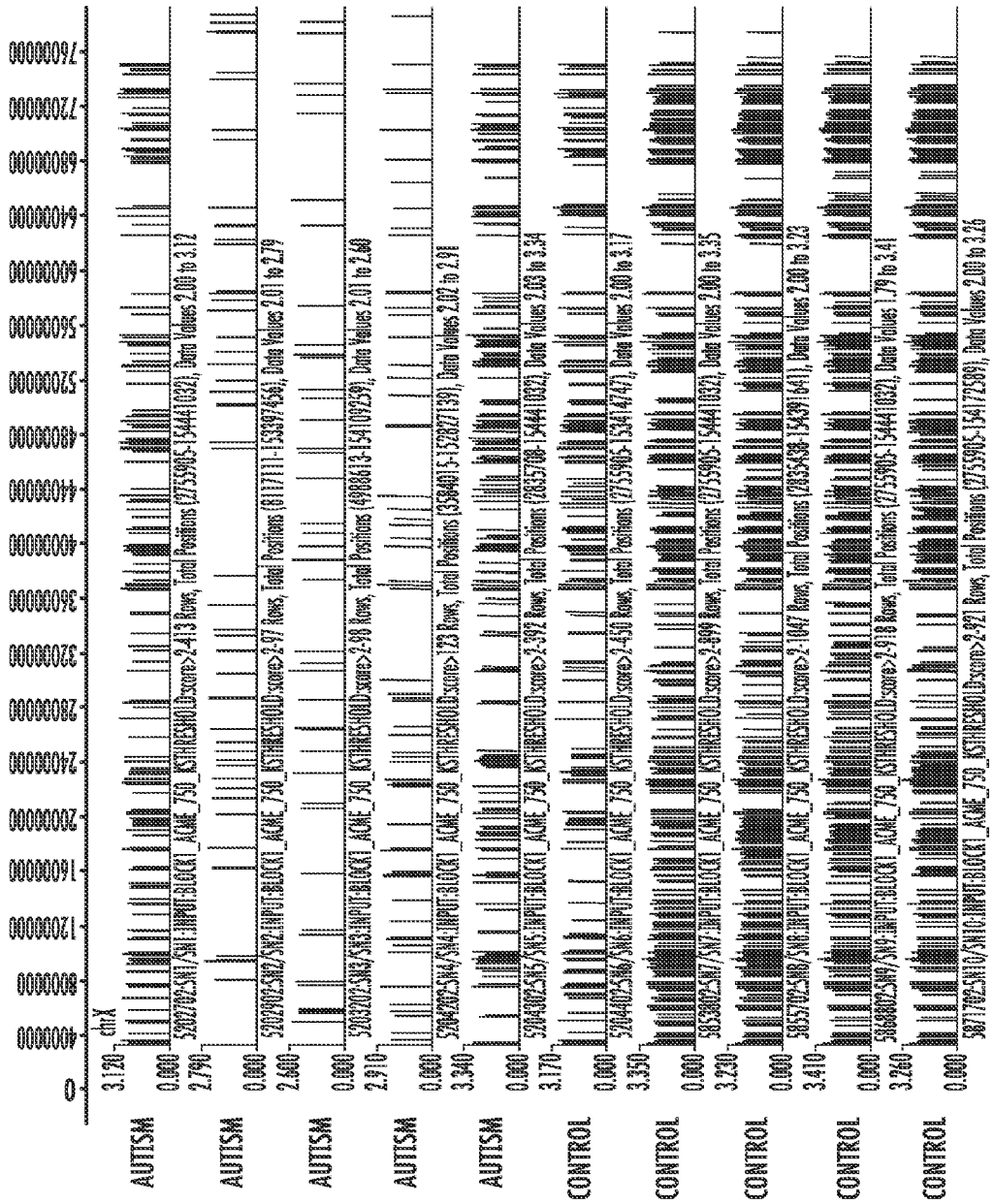
FIG. 1 represents data showing the overall methylation level of the entire X-chromosome for 5 individuals diagnosed with ASD and the overall methylation level of the entire X-chromosome for 5 individuals not affected with ASD.

As used herein, the terms "autism" and "autism spectrum disorders" (ASD) are used interchangeably to generally describe three of the five pervasive developmental disorders described in the Diagnostic and Statistical Manual, IVth Edition (DSM IV-TR), the disclosure of which is hereby incorporated by reference: autistic disorder, Asperger disorder, and pervasive developmental disorders (American Psychiatric Association 2000). The clinical hallmarks of autism include disturbances in three categories of behavior—reciprocal social interactions, verbal and nonverbal communications, and age appropriate activities and interests. Mental retardation coexists in over two-thirds of individuals with autism spectrum disorder but is conspicuously absent in Asperger disorder. The other neurological manifestation of note is seizures, which occur in 20-35 percent of individuals with autism spectrum disorders.

The physical appearance of, individuals with autism is generally unremarkable, characterized by normal facial appearance, musculoskeletal structures, internal organs, and sexual development. Intrauterine and postnatal growth usually follows a normal course. A subgroup of approximately 20% of individuals with autism has macrocephaly, which is usually acquired during the first four years of life. Generalized brain overgrowth and cerebellar hypoplasia have been found in some cases using brain-imaging techniques, Reduced Purkinje cell counts in the cerebellum, reduced neuron size and absence of gliosis have been noted on brain microscopy.

Because of the absence of consistent physical findings in autism and the uncertainty of the diagnosis in the first couple of years of life, a laboratory test that helps diagnose autism at an early age would be desirable.

As used herein, the term "normal" with regard to level of expression of a gene generally refers to the average level of expression of a gene in individuals not affected by any autism spectrum disorders.

"Overexpression" and "underexpression" of a gene refer to expression of the gene at a greater or lesser level, respectively, than normal level of expression of the gene.

As used herein the term "promoter sequence" generally refers to a nucleic acid sequence which is required for expression of a gene product. In some instances, this sequence may be the core promoter sequence and in other instances, this sequence may also include an enhancer sequence and other regulatory elements which are required for expression of the gene product.

As used herein, the term "transcribed polynucleotide" generally refers to a polynucleotide (e.g. an RNA, a cDNA, or an analog of one of an RNA or cDNA) which is complementary to or homologous with all or a portion of a mature RNA made by transcription of a genomic DNA and normal post-transcriptional processing (e.g. splicing), if any, of the transcript.

As used herein, the terms "hypermethylated" and "hypermethylation" generally refer to excessive (e.g., more than the methylation of the same gene from a non-affected person or group of non-affected persons) methylation of one or more cytosines within or flanking genes. In one particular embodiment, the one or more cytosines are at CpG dinucleotides, but this is not a requirement of the term. Hypermethylation is a recognized epigenetic mechanism for suppression of gene expression (Grant 2008, Wilson et al. 2006). This is true for X-linked genes known to be down-regulated during the course of X-inactivation.

Conversely, the terms "hypomethylated" and "hypomethylation" generally refer to undermethylation (e.g., less than the methylation of the same gene from a non-affected person or group of non-affected persons) of one or more cytosines within or flanking genes, for instance at CpG dinucleotides. The expression of X-linked genes may be increased (i.e., overexpressed) if CpGs associated with the genes are hypomethylated.

As used herein, the terms "affected" and "affected person" generally refer to a person with features of autism or autism spectrum disorders as defined by The American Psychiatric Association (2000). While males are more commonly affected with autism spectrum disorders, both males and females may be affected. Conversely, the terms "non-affected" and "non-affected person" refers to a person without features of autism or autism spectrum disorders as defined by The American Psychiatric Association (2000).

As used herein the term "marker" generally refers to a material that can be used to directly or indirectly identify predisposition of an individual for ASD as well as to directly or indirectly identify an individual affected with ASD. For example, markers include, without limitation, DNA methylation of sense and anti-sense strands of genomic DNA (optionally including any introns occurring therein), RNA generated by transcription of genomic DNA, RNA generated by splicing of RNA transcribed from genomic DNA, and proteins or portions thereof (including proteins both before and after cleavage of normally cleaved regions such as transmembrane signal sequences). As used herein, "marker" may also include a cDNA made by reverse transcription of an RNA generated by transcription of genomic DNA (including spliced RNA).

As used herein, the term "probe" generally refers to any molecule which is capable of binding to a specifically intended target molecule, e.g., a marker. Probes can be either synthesized or derived from natural materials. Examples of molecules that can be utilized as probes include, but are not limited to, RNA, DNA, proteins, antibodies, and organic monomers.

As used herein, the term "gene" generally refers to a locatable region of a genomic sequence that is involved in producing a polypeptide chain, and includes regulatory regions, introns, transcribed regions and/or other functional sequence regions. The term also refers to sequences that are transcribed but not translated into a polypeptide (e.g., noncoding microRNAs).

As utilized herein, the term "flanking sequences" generally refers to sequences that are located on either end of a coding region, usually within 500 Kb of coding region. Flanking sequences are located 5' or 3' to the translated sequences. The 5' flanking region may contain control or regulatory sequences such as promoters and enhancers or other recognition or binding sequences for proteins that control or influence the transcription of the gene. The 3' flanking region may contain sequences that direct the termination of transcription, post-transcriptional cleavage and polyadenylation as well as recognition sequences for other proteins.

The terms "protein," "peptide" and "polypeptide" are used interchangeably herein.

As used herein, the term "hybridization" generally refers to the process of annealing complementary nucleic acid strands by forming hydrogen bonds between nucleotide bases on the complementary nucleic acid strands. Hybridization, and the strength of the association between the nucleic acids, is impacted by such factors as the degree of complementarity between the hybridizing nucleic acids, the stringency of the conditions involved, the melting temperature ($T_m$) of the formed hybrid, the length of the hybridizing nucleic acids and the G:C ratio of those nucleic acids.

DETAILED DESCRIPTION

Reference now will be made to the embodiments of the disclosure, one or more examples of which are set forth below. Each example is provided by way of an explanation of the disclosure, not as a limitation of the disclosure. In fact, it will be apparent to those skilled in the art that various modifications and variations can be made in the disclosure without departing from the scope or spirit of the disclosure. For instance, features illustrated or described as one embodiment can be used on another embodiment to yield still a further embodiment. It is to be understood by one of ordinary skill in the art that the present discussion is a description of exemplary embodiments only, and is not intended as limiting the broader aspects of the present disclosure, which broader aspects are embodied exemplary constructions.

Disclosed herein is the discovery that alterations in methylation on the X chromosome, which can cause one or more genes on the single X chromosome in males to be partially or totally silenced or overexpressed, can constitute a predisposition to autism spectrum disorders and other related neurobehavioral conditions to include, but not limited to, mental retardation, attention deficit hyperactivity disorders, and learning disabilities.

Generally speaking, the present disclosure is directed to methods for determining whether one or more brain expressed genes located on the X chromosome are hypomethylated or hypermethylated and the subsequent predisposition for or diagnosis of ASD. More specifically, it has been determined that hypermethylation or hypomethylation of brain expressed genes can signify a predisposition to autism.

Possession of but a single X chromosome imposes on males a biological inequity which places them at higher risk than females for a number of health maladies. While the inactivation of one of the two X chromosomes in females makes a single active X chromosome the norm in both sexes, this phenomenon clearly does not compensate for the inequity. Nowhere has this inequity been studied more extensively than in X-linked mental retardation (XLMR). Overall, about 30% more males than females will have mental retardation and at least some portion of this excess can be attributed to X-linked genes. Ten to twelve percent of all mental retardation appears to be X-linked.

In one embodiment, the overall methylation level of the X-chromosome can be examined to determine the predisposition of an individual for ASD. According to this embodiment, a statistically different degree of overall methylation of the X chromosome can be a signal for ASD. For instance, an individual exhibiting an overall difference in methylation (i.e., any combination of overmethylation and/or undermethylation) of the X-chromosome of more than about 20%, or more than about 33% in another embodiment, as compared to normal methylation levels can be predisposed to or affected with ASD.

Alternatively, a smaller group of genes can be the basis for disclosed determinations. For example, in one embodiment, genes encompassed by the present disclosure include those that are 1) located on the X chromosome, 2) expressed in the brain, 3) subject to inactivation, and 4) associated with mental retardation or autism.

Currently, 87 brain expressed genes have been identified (Table 1, below) as candidate genes for disclosed determinations. However, the present disclosure is not limited to these specific 87 brain expressed genes. In particular, it is believed that hypermethylation or hypomethylation of any gene or group of genes on the X chromosome can be a marker for the diagnosis of autism in an individual.

By extension, overexpression or underexpression of such genes and increased or decreased production of proteins encoded by such genes can be a designation for the diagnosis of autism.

Figure 2:
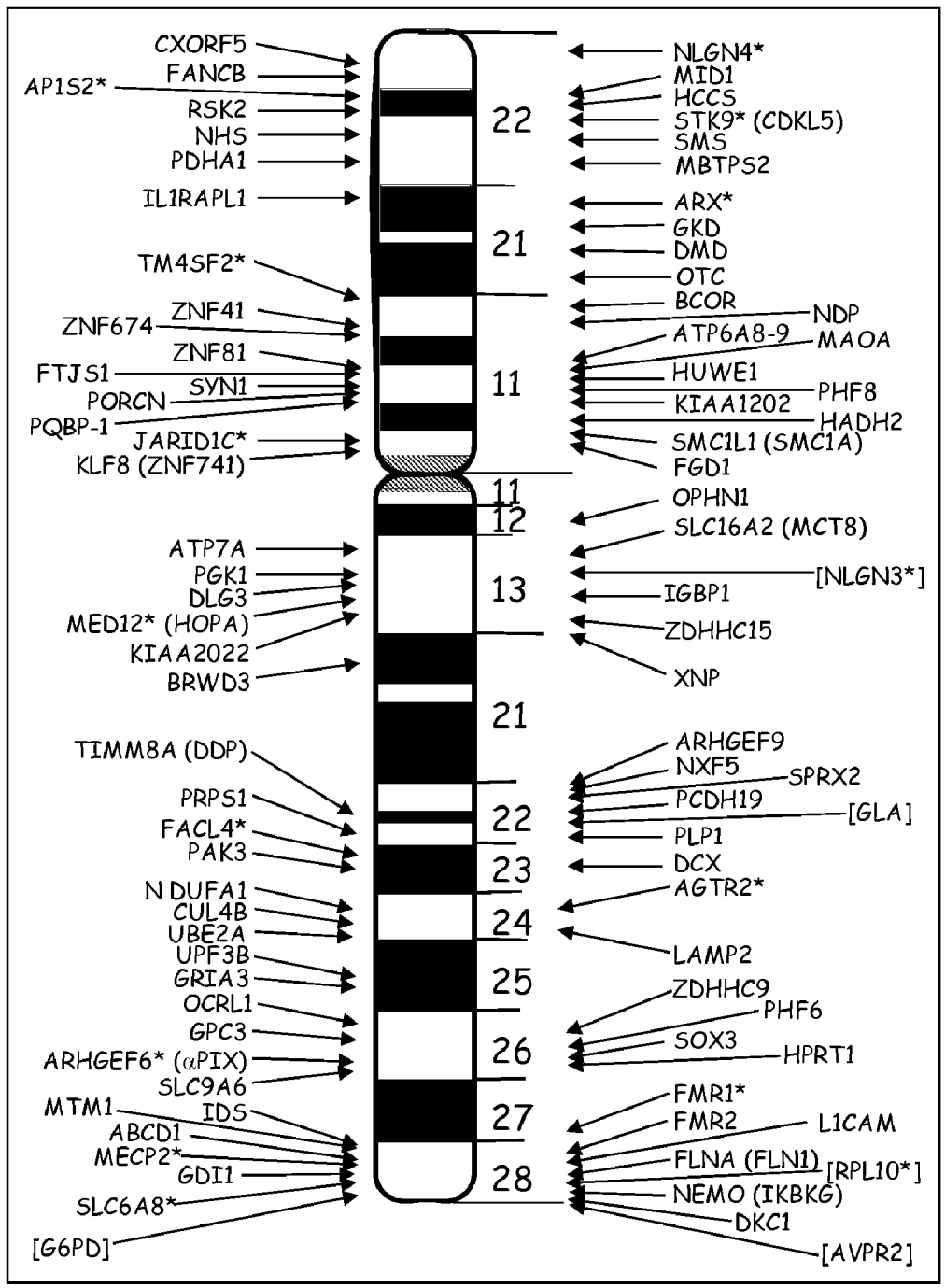
FIG. 2 represents an ideogram of the X chromosome showing the location of the currently known 85 brain expressed genes that can be a factor in development of autism when hypermethylated or hypomethylated. In addition, the location of two housekeeping genes, [G6PD, GLA], two autism genes [NLGN3, RPL10], and one gene [AVPR2] of uncertain significance are shown in brackets.

Table 1 and FIG. 2 identify the name, symbol and location of 87 brain expressed genes on the X chromosome encompassed by the present disclosure. Ordinary mutations (e.g., changes in the coding sequence of the genes) in 85 of these 87 genes have been previously linked to mental retardation. Also, mutations in 15 of these 85 X-linked mental retardation (XLMR) genes have been associated with autism or autistic behaviors in addition to mental retardation. These 15 are identified with an asterisk in Table 1 and FIG. 2. Data on these genes are available with reference to R. E. Stevenson, C. E. Schwartz, and R. J. Schroer, "Atlas on X-Linked Mental Retardation" (X-Linked Mental Retardation, Oxford University Press, 2000) and the XLMR Update located at http://www.ggc.org/xlmr.htm, which are incorporated by reference herein. Additional data on these and other genetic and proteinaceous material discussed herein are available through the National Center for Biotechnology Information. The disorders associated with usual mutations in each gene and the currently known function(s) of each gene are also listed in Table 1.

TABLE 1

| Gene Symbol | Gene Name | Gene Location | XLMR Entity | Function |
| --- | --- | --- | --- | --- |
| α-PIX* (ARHGEF6) | Rho guanine nucleotide exchange factor 6 | Xq26.3 | MRX46 | Effector of the rho GTPases |
| AGTR2* | Angiotensin-II receptor type 2 | Xq23 | XLMR-optic atrophy, MRX | Angiotensin II receptor |
| ALDP (ABCD1) | Adrenoleukodystrophy protein | Xq28 | Adrenoleukodystrophy | Peroxisomal transport protein |
| AP1S2* | Sigma 2 subunit of adaptor protein/complex | Xp22.2 | Turner, XLMR-hydrocephaly-basal ganglia calcification | Assembly of endocytic vesicles |
| ARHGEF9 | Rho guanine nucleotide exchange factor 9 | Xq11.2 | XLMR-hypotonia seizures | Regulation of Rho protein signal transduction |
| ARX* | Aristaless-related X chromosome gene | Xp22.11 | Hydranencephaly, Partington, Proud, West, X-linked lissencephaly with abnormal genitalia, MRX29, 32, 33, 36, 43, 54, 76 | Neuronal migration |

TABLE 1-continued

| Gene Symbol | Gene Name | Gene Location | XLMR Entity | Function |
|---|---|---|---|---|
| ATP6A8-9 (ATP6AP2) | Renin receptor | Xp11.4 | XLMR-infantile epilepsy | Renin receptor |
| ATP7A | Copper transporting ATPase 7A | Xq21.1 | Menkes, occipital horn | Copper transport |
| BCOR | BCL6 corepressor | Xp11.4 | Lenz microphthalmia (1 type) | Histone/protein deacetylation |
| BRWD3 | Bromodomain and WD repeat domain-containing protein 3 | Xq21.1 | XLMR-macrocephaly-large ears | Transcription factor |
| CUL4B | Cullin 4B | Xq24 | XLMR-hypogonadism-tremor | Cell cycle, ubiquitin cycle, E3 ubiquitin ligase |
| DCX | Doublecortin | Xq23 | X-linked lissencephaly | Neuronal migration |
| DDP (TIMM8A) | Dystonia-deafness peptide | Xq22.1 | Mohr-Tranebjaerg, Jensen | Transcription factor |
| DKC1 | Dyskerin | Xq28 | Dyskeratosis congenita | Cell cycle and nucleolar functions |
| DLG3 | Neuroendocrine DLG | Xq13.1 | MRX | NMDA-receptor, mediated signaling, synaptic plasticity |
| DMD | Dystrophin | Xp21.2-p221.1 | Duchenne | Structure of skeletal muscle membrane |
| FACL4* (ACSL4) | Fatty acid acyl CoA synthetase type 4 | Xq23 | MRX63, 68 | Fatty acid CoA ligase 4 |
| FANCB | Fanconi anemia complementation group B protein | Xp22.2 | X-linked VACTERL-hydrocephaly | DNA repair |
| FGD1 (FGDY) | Faciogenital dysplasia | Xp11.22 | Aarskog-Scott | Guanine nucleotide exchange factor |
| FLNA (FLN1) | Filamin 1 | Xq28 | Epilepsy with periventricular heterotopia | Actin-binding protein |
| FMR1* | Fragile X mental retardation 1 | Xq27.3 | Fragile X | RNA binding protein, gene regulation |
| FMR2 | Fragile X mental retardation 2 | Xq28 | Fragile XE | Unknown |
| FTSJ1 | Methyl transferase | Xp11.23 | MRX9 | Methylase |
| GDI1 | Rab GDP-dissociation inhibitor 1 | Xq28 | MRX41, 48 | Stabilizes GDP bound conformations |
| GKD | Glycerol kinase deficiency | Xp21.2 | Glycerol kinase deficiency | Metabolism, glycerol uptake |
| GPC3 | Glypican 3 | Xq26.2 | Simpson-Golabi-Behmel | Cell adhesion, motility |
| GRIA3 | Glutamate receptor ionotropic AMPA 3 | Xq25 | Chiyonobu XLMR | Signal transduction, ion transport, glutamate signaling pathway |
| HADH2 | Hydroxyacyl-coenzyme A dehydrogenase, type III | Xp11.22 | XLMR-choreoathetisis | Lipid metabolism |
| HCCS | Holocytochrome C synthase | Xp22.2 | MIDAS syndrome | Energy production, cytochrome homolyase |
| HPRT | Hypoxanthine guanine phosphoribosyl transferase | Xq26.2 | Lesch-Nyhan | Enzyme |
| HUWE1 | E3 ubiquitin-protein ligase | Xp11.22 | MRX | Ubiquitin-protein ligase, mRNA transport |
| IDS | Iduronate sulfatase | Xq28 | Hunter | Lysosomal enzyme |
| IGBP1 | Immunoglobulin-binding protein 1 | | Graham coloboma | |
| IL1RAPL | IL-1 receptor accessory protein-like | Xp21.2 | MRX34 | Unknown |
| JARID1C* | Jumonji, AT-rich interactive domain 1C | Xp11.22 | MRX | Regulates transcription, chromatin remodeling |
| KIAA1202 (SHROOM4) | KIAA1202 protein | Xp11.22 | Stoccos dos Santos | Roles in cellular architecture, neurulation, and ion channel function |
| KIAA2022 | KIAA2022 protein | Xq13.2 | Cantagrel spastic paraplegia | DNA synthesis, DNA polymerase activity |
| KLF8 (ZNF741) | Kruppel-like factor 8 | Xp11.21 | MRX | |
| L1CAM | Cell adhesion molecule, L1 | Xq28 | XLHS, MASA, XL-ACC, SPG2 | Neuronal migration, cell adhesion |
| LAMP2 | Lysosomal associated membrane protein 2 | Xq24 | Danon cardiomyopathy | Membrane, lysosome |
| MAOA | Monoamine oxidase A | Xp11.3 | Monoamine oxidase A deficiency | Enzyme |

TABLE 1-continued

| Gene Symbol | Gene Name | Gene Location | XLMR Entity | Function |
|---|---|---|---|---|
| MBTPS2 | Intramembrane zinc metalloprotease | Xp22.1 | Ichthyosis follicularis, atrichia, photophobia | Protease activity, activates signaling proteins |
| MECP2* | Methyl-CpG binding protein 2 | Xq28 | Rett, MRX16, 79 | Binds methylated CpGs |
| MED12* (HOPA) | Mediator of RNA polymerase II transcription, subunit 12 | Xq13.1 | Opitz FG syndrome, Lujan syndrome | Transcription regulation, RNA polymerase II transcription mediator activity, ligand-dependent nuclear receptor transcription coactivator activity, vitamin D receptor and thyroid hormone receptor binding |
| MID1 | Midline 1 | Xp22.2 | Opitz G/BBB | Zinc finger gene |
| MTM1 | Myotubularin | Xq28 | Myotubular myopathy | Tyrosine phosphatase |
| NDP | Norrie | Xp11.3 | Norrie | Neuroectodermal cell interaction |
| NDUFA1 | NADH dehydrogenase (ubiquinone) 1 alpha subcomplex | Xq24 | Mitochondrial complex 1 deficiency | Energy production, oxidoreductase activity |
| NEMO (IKB6KG) | NF-$_K$B essential modulator | Xq28 | Incontinentia pigmenti | Activates the transcription factor NF-$_K$B |
| NHS | Nance-Horan syndrome gene | Xp22.2-22.13 | Nance-Horan | — |
| NLGN3* | Neuroligin 3 | Xq13.1 | Autism | Cell adhesion |
| NLGN4* | Neuroligin 4 | Xp22.32-22.31 | Autism | Cell adhesion |
| NXF5 | Nuclear RNA export factor 5 | Xq22.1 | XLMR-short stature-muscle wasting | mRNA processing, mRNA export from nucleus |
| OCRL1 | Oculorenal | Xq25 | Lowe | Enzyme |
| OFD1 | Oral-facial-digital syndrome 1 | Xp22.2 | Oral-facial-digital 1 | Unknown |
| OPHN1 | Oligophrenin 1 | Xq12 | MRX60 | GTPase activating protein |
| OTC | Ornithine transcarbamylase | Xp11.4 | Ornithine transcarbamylase deficiency | Enzyme |
| PAK3 | P21-activated kinase | Xq23 | MRX30, 47 | Rac/Cdc 42 effector |
| PCDH19 | Protocadherin 19 | Xq22 | Epilepsy and mental retardation limited to females | |
| PDHA1 | Pyruvate dehydrogenase | Xp22.12 | Pyruvate dehydrogenase deficiency | Enzyme |
| PGK1 | Phosphoglycerokinase 1 | Xq13.3 | Phosphoglycerokinase deficiency | Enzyme |
| PHF6 | PHD-like zinc finger gene 6 | Xq26.2 | Börjeson-Forssman-Lehmann | Unknown |
| PHF8 | PFD finger protein 8 | Xp11.22 | XLMR-clefting | Regulates transcription, binds DNA |
| PLP | Proteolipid protein | Xq22.2 | PMP, SPG1 | Myelination |
| PORCN | *Drosophila* porcupine homolog | Xp11.23 | Goltz syndrome | Wnt receptor signaling pathway, acryl-transferase activity, integral to membrane of endoplasmic reticulum |
| PQBP1 | Polyglutamine tract binding protein 1 | Xp11.23 | Renpenning, Sutherland-Haan, Hamel cerebro-palatocardiac, Golabi-Ito-Hall, Porteous, MRX55 | Polyglutamine binding, regulates transcription |
| PRPS1 | Phosphoribosyl pyrophosphate synthetase 1 | Xq22.3 | Arts syndrome, PRPS1 superactivity | Ribonucleotide monophosphate biosynthesis |
| RPL10* | Ribosomal protein L10 | Xq28 | Autism | Protein synthesis, ribosomal protein |
| RSK2 | Threonine-serine kinase 2 | Xp22.12 | Coffin-Lowry, MRX19 | Kinase signaling pathway |
| SLC16A2 (MCT8) | T3 transporter | Xq13.2 | Allan-Herndon-Dudley | T3 receptor |

TABLE 1-continued

| Gene Symbol | Gene Name | Gene Location | XLMR Entity | Function |
|---|---|---|---|---|
| SLC6A8* | Creatine transporter | Xq28 | XLMR with seizures | Creatine transporter |
| SLC9A6 | Sodium-hydrogen exchanger NHE6 | Xq26.3 | Christianson, X-linked Angelman-like syndrome | Sodium-hydrogen antiporter activity, lysosome organization and biogenesis, regulation of endosome volume |
| SMC1A/ SMC1L1 | SMC1 structural maintenance of chromosomes 1-like | Xp11.22 | X-linked Cornelia de Lange syndrome | Cell cycle, mitotic spindle organization and biogenesis, chromosome segregation |
| SMS | Spermine synthase | Xp22.11 | Snyder-Robinson | Synthesis of spermine |
| SOX3 | SRY-box 3 | Xq27.1 | XLMR-growth hormone deficiency | Pituitary function, transcription factor |
| SRPX2 | Sushi repeat containing protein, X-linked | Xq22.1 | XLMR-Rolandic epilepsy-speech dyspraxia | Signal transduction, growth factor 2 |
| STK9* (CDKL5) | Serine-threonine kinase 9 | Xp22.12 | XLMR with seizures Rett-like | Unknown |
| SYN1 | Synapsin 1 | Xp11.23 | Epilepsy-macrocephaly | Synaptic vesicle protein |
| TM4SF2* | Transmembrane 4 superfamily member 2 | Xp11.4 | MRX58 | Interacts with integrins |
| UBE2A | Ubiquitin-conjugating enzyme E2A | Xq24 | XLMR-nail dystrophy-seizures | Ubiquitin cycle, ubiquitin-protein ligase |
| UPF3B | UPF3 regulator of nonsense transcript homolog B | Xq24 | MRX, Lujan/FG phenotype | mRNA catabolism, nonsense mediated decay |
| XNP (XH2, ATRX) | X-linked nuclear protein, X-linked helicase 2 | Xq21.1 | α-thalassemia mental retardation, Carpenter-Waziri, Chudley-Lowry, Holmes-Gang, Juberg-Marsidi, XLMR-hypotonic facies, XLMR-spastic paraplegia | Transcription factor, helicase activities, |
| ZDHHC9 | Zinc finger, DHHC-domain containing protein 9 | Xq25-Xq26.1 | XLMR-macrocephaly-Marfanoid habitus | ? |
| ZDHHC15 | Zinc finger DHHC domain-containing protein 15 | Xq13.3 | MRX91 | |
| ZNF41 | Zinc finger 41 | Xp11.3 | MRX | Zinger finger |
| ZNF674 | Zinc finger protein 674 | Xp11.3 | XLMR-retinal dystrophy-short stature and MRX | Transcription regulation |
| ZNF81 | Zinc finger 81 | Xp11.23 | MRX45 | Zinc finger |

Hypomethylation or hypermethylation of these 87 brain expressed genes or flanking regions of these 87 genes (85 XLMR genes plus NLGN3 and RPL10) singly or in combination may predispose to autism, whereas usual mutations in the 85 XLMR genes (e.g., changes in the coding sequence of the genes) cause mental retardation. For instance, when examining any group of three or more X-chromosome genes and flanking regions thereof, either hypomethylation or hypermethylation of at least about 20% of the group can be evidence of a predisposition to or diagnosis of ASD. Of course, larger groups of genes are encompassed in the disclosure as well. By way of example, any group of seven, ten, or more of genes on the X chromosome and corresponding flanking regions can be examined, and either hypomethylation or hypermethylation of at least about 20% of the group can be evidence of a predisposition to or diagnosis of ASD. Moreover, it should be noted that hypomethylation or hypermethylation of a larger percentage of any examined group of genes can also signal the predisposition to or diagnosis of ASD. For instance, evidence of either hypomethylation or hypermethylation on at least about 50%, 60%, 70% or 80% of an examined group of genes can be evidence of a predisposition to or actually affected with ASD.

The distribution of the XLMR genes of Table 1 on the X chromosome is shown in FIG. 2. Specifically, FIG. 2 shows an ideogram that identifies and shows the location of the exemplary brain-expressed genes on the X chromosome which may predispose to autism when hypermethylated or hypomethylated. Two housekeeping genes, G6PD and GLA, which are used as controls, are also shown in brackets. Two autism genes, NLGN3 and RPL10, are also shown in brackets. The location of AVPR2, an X-linked gene of uncertain importance in autism and mental retardation, is also shown in brackets.

According to the present disclosure, any suitable method can be used for detecting the presence of hypomethylation or hypermethylation of brain expressed gene(s) in an individual. Suitable methods for detecting altered methylation of brain expressed genes on the X chromosome, include, but are not limited to, DNA bisulfite sequencing, pyrosequencing, polymerase chain reaction (PCR)/digestion with restriction endonucleases, methylation-specific PCR, real-time PCR, Southern blot analysis, mass spectrometry, multiplex ligation-dependent probe amplification (MLPA), chromatin immunoprecipitation (ChIP), methylation microarray, high performance liquid chromatography (HPLC), high performance capillary electrophoresis (HPCE), methylation-sensitive single-nucleotide primer extension, methylation-sensitive single-stranded conformational polymorphism, methylation-sensitive restriction endonucleases, ligation mediated PCR, methylation-specific in situ hybridization, incomplete primer extension mixture, competitive primer binding site analysis, solid-phase primer extension, denaturing gradient gel electrophoresis, enzymatic regional methylation assay, combined bisulfite restriction analysis (COBRA), methylLight, and the like.

For example, one particular embodiment involves comparing the degree of methylation (methylation value) of a specific CpG dinucleotide associated with a particular gene of an individual to be tested to a pre-determined range of methylation values of that particular CpG site from a control group of non-affected persons. The pre-determined range can be, for example within one standard deviation of the average value of that particular CpG site found in the control group. The methylation value of the particular CpG site can readily be determined according to methods well known to one of ordinary skill in the art. If the methylation value falls outside of this pre-determined range, then the person from which the tested CpG site originated may be predisposed to or even suffering from undiagnosed autism. This type of "positive" result can alert the tester, doctors, parents, and other caregivers that the person has an increased likelihood of developing autism or its symptoms. At a minimum, a "positive" result can indicate that the individual is a candidate for additional testing for autism.

One method of comparing the methylation value of a particular CpG site of an individual to a pre-determined range of methylation values of that particular CpG site from a control group of non-affected persons involves plotting the methylation value of the sample CpG site against a scatterplot of the methylation values of that particular CpG site taken from a plurality of non-affected persons. For example, a plot can be used to create a chart having on the X-axis the age of the person from which the DNA originated and on the Y-axis the methylation value of the CpG site being analyzed. When analyzing the resulting scatterplot chart, if the methylation value of the patient falls above or below the methylation values of non-affected persons, then the tested CpG site may be from an individual that is predisposed to or even suffering from undiagnosed autism. By way of example, if the methylation value of the tested individual is statistically different (e.g., P value of $\leq 0.05$) from the average methylation value of the comparison data, then the individual may be predisposed to or affected with ASD.

When conducting a comparison of the methylation value of a particular CpG site from an individual against those values of that CpG site taken from a control group of non-affected persons, the number of controls (non-affected persons) may vary, as is generally known in the art. However, in order to be of increased value, a statistically significant number of controls are generally utilized. For instance, at least about 2 controls can be utilized. In other embodiments, more controls such as about 10, about 25, about 40 or about 100 controls can be utilized to create a suitable range of methylation values for a particular CpG site.

In general, ASD affected persons have more than one hypermethylated or hypomethylated X-linked gene. As such, the more hypermethylated or hypomethylated genes that a person has, the more likely the chances of that person developing autism. Thus, a comparison of methylation values of CpG sites associated with several genes from the same person, as discussed above, can be effective in determining the predisposition of that person to autism.

It is well established that the level of expression of X chromosome genes is correlated with and perhaps even controlled by methylation of CpG sites in the promoter regions (see, e.g., Chen and Li, 2006, *Curr To. Microbiol Immunol*, 301:179-201; Wilson, et al., *Biochim Biophys Acta*, 1775: 138-162; both of which are incorporated herein by reference). Moreover, it is believed that in males even subtle alterations in normal methylation patterns may significantly affect transcriptional efficiency, and this may be particularly important in brain tissue, where tighter gene regulation can be expected. Furthermore, it is apparent that the methylation status of key CpG's may actually act as a switch for expression efficiency regardless of the status of other possible sites of methylation.

Accordingly, in conjunction with or alternative to determining the methylation level of genes in determination of predisposition to or diagnosis of ASD, the present disclosure is also directed to detecting overexpression or underexpression of X-chromosome genes in an individual. For instance, disclosed herein is a method including determining the expression level of a group of three or more X-chromosome genes, wherein a significantly different expression level between tested samples and control samples indicates a predisposition to or diagnosis of ASD.

In one embodiment, the present disclosure is directed to microarrays that can be used to determine the expression level of genes to indicate a predisposition to or diagnosis of ASD. Beneficially, disclosed arrays can be particularly designed to examine RNA from cell culture or from native lymphocytes for overexpression or underexpression of predetermined gene sets associated with ASD. For example, according to disclosed methods, an array, e.g., an oligo microarray or a PCR array, can be used to determine expression levels with emphasis on a specified set of genes as disclosed herein.

Through comparison of the gene expression level of human lymphoblast cells with controls, exemplary protocols of which are described in the Example section, below, 44 X chromosome genes have been determined to exhibit significant differences in expression in affected individuals (Table 2, below).

TABLE 2

| Gene | Name | Functional Description | Location | Autism/Control |
|------|------|------------------------|----------|----------------|
| ELK1 | ELK1, member of ETS oncogene family | nuclear target for the ras-raf-MAPK signaling cascade | Xp11.2 | 1.2 |
| PLP2 | proteolipid protein 2 (colonic epithelium-enriched) | unknown | Xp11.23 | 0.8 |
| PQBP1 | polyglutamine binding protein 1 | PQBP1 is a nuclear polyglutamine-binding protein that contains a WW domain | Xp11.23 | 1.3 |

TABLE 2-continued

| Gene | Name | Functional Description | Location | Autism/Control |
|---|---|---|---|---|
| ZNF81 | zinc finger protein 81 | unknown | Xp11.23 | 1.4 |
| CFP | complement factor properdin | active in the alternative complement pathway of the innate immune system | Xp11.3-p11.23 | 1.4 |
| DDX3X | DEAD (Asp-Glu-Ala-Asp) box polypeptide 3, X-linked | involving alteration of RNA secondary structure such as translation initiation, nuclear and mitochondrial splicing, and ribosome and spliceosome assembly | Xp11.3-p11.23 | 1.2 |
| CASK | calcium/calmodulin-dependent serine protein kinase (MAGUK family) | calcium/calmodulin-dependent serine protein kinase; member of the membrane-associated guanylate kinase (MAGUK) protein family; scaffolding proteins associated with intercellular junctions | Xp11.4 | 0.7 |
| RP2 | retinitis pigmentosa 2 (X-linked recessive) | cause of X-linked retinitis pigmentosa; may be involved in beta-tubulin folding. | Xp11.4-p11.21 | 1.2 |
| DMD | dystrophin | responsible for Duchenne (DMD) and Becker (BMD) Muscular Dystrophies; dystrophin (as encoded by the Dp427 transcripts) is a large, rod-like cytoskeletal protein which is found at the inner surface of muscle fibers; dystrophin is part of the dystrophin-glycoprotein complex (DGC), which bridges the inner cytoskeleton (F-actin) and the extra-cellular matrix | Xp21.2 | 0.6 |
| CDKL5 | cyclin-dependent kinase-like 5 | Ser/Thr protein kinase; mutations associated with X-linked infantile spasm syndrome (ISSX); also known as X-linked West syndrome and Rett syndrome (RTT) | Xp22 | 1.5 |
| MID1 | midline 1 (Opitz/BBB syndrome) | may act as anchor points to microtubules; mutations associated with the X-linked form of Opitz syndrome, which is characterized by midline abnormalities such as cleft lip, laryngeal cleft, heart defects, hypospadias, and agenesis of the corpus callosum | Xp22 | 0.7 |
| MAP7D2 | MAP7 domain containing 2 | unknown | Xp22.12 | 0.3 |
| GPR64 | G protein-coupled receptor 64 | unknown | Xp22.13 | 0.6 |
| SCML1 | sex comb on midleg-like 1 (Drosophila) | unknown | Xp22.2-p22.1 | 0.6 |
| CLCN4 | chloride channel 4 | unknown but may contribute to the pathogenesis of neuronal disorders | Xp22.3 | 2.7 |
| AMELX* | amelogenin (amelogenesis imperfecta 1, X-linked) | amelogenin family of extracellular matrix proteins; involved in biomineralization during tooth enamel development; mutations cause X-linked amelogenesis imperfecta | Xp22.31-p22.1 | 0.8 |
| WWC3 | WWC family member 3 | unknown | Xp22.32 | 2.4 |
| ARHGEF9 | Cdc42 guanine nucleotide exchange factor (GEF) 9 | Rho-like GTPases that act as molecular switches by cycling from the active GTP-bound state to the inactive GDP-bound state; regulators of the actin cytoskeleton and cell signaling | Xq11.1 | 1.4 |
| FLJ44635 | TPT1-like protein | unknown | Xq13.1 | 1.3 |
| NLGN3 | neuroligin 3 | neuronal cell surface protein; may act as splice site-specific ligand for beta-neurexins and may be involved in the formation and remodeling of central nervous system synapses; mutations in this gene may be associated with autism and Asperger syndrome | Xq13.1 | 1.3 |
| KIF4A | kinesin family member 4A | microtubule-based motor proteins that generate directional movement along microtubules | Xq13.1 | 0.8 |
| KIAA2022 | KIAA2022 | unknown | Xq13.3 | 1.6 |
| RNF12 | ring finger protein 12 | ubiquitin protein ligase that targets LIM domain binding 1 (LDB1/CLIM) and causes proteasome-dependent degradation of LDB1 | Xq13-q21 | 1.2 |
| ZMAT1 | zinc finger, matrin type 1 | unknown | Xq21 | 0.6 |
| DIAPH2 | diaphanous homolog 2 (Drosophila) | defects in this gene have been linked to premature ovarian failure 2 | Xq21.33 | 0.8 |
| GPRASP1 | G protein-coupled receptor associated sorting protein 1 | unknown | Xq22.1 | 1.2 |
| CXorf39 | chromosome X open reading frame 39 | unknown | Xq22.2 | 1.2 |
| NUP62CL | nucleoporin 62 kDa C-terminal like | unknown | Xq22.3 | 0.7 |

TABLE 2-continued

| Gene | Name | Functional Description | Location | Autism/Control |
|------|------|------------------------|----------|----------------|
| TBC1D8B | TBC1 domain family, member 8B (with GRAM domain) | unknown | Xq22.3 | 0.7 |
| AGTR2* | angiotensin II receptor, type 2 | plays a role in the central nervous system and cardiovascular functions that are mediated by the renin-angiotensin system; this receptor mediates programmed cell death (apoptosis). | Xq22-q23 | 0.8 |
| AMOT | angiomotin | may mediate the inhibitory effect of angiostatin on tube formation and the migration of endothelial cells toward growth factors during the formation of new blood vessels | Xq23 | 1.9 |
| KLHL13 | kelch-like 13 (*Drosophila*) | unknown | Xq23-q24 | 1.4 |
| LONRF3 | LON peptidase N-terminal domain and ring finger 3 | may be involved in protein-protein and protein-DNA interaction | Xq24 | 0.7 |
| WDR44 | WD repeat domain 44 | unknown | Xq24 | 1.3 |
| UTP14A | UTP14, U3 small nucleolar ribonucleoprotein, homolog A (yeast) | unknown | Xq25 | 1.3 |
| SH2D1A* | SH2 domain protein 1A | plays a major role in the bidirectional stimulation of T and B cells; acting as an inhibitor of the signaling lymphocyte-activation molecule; mutations in this gene cause lymphoproliferative syndrome X-linked type 1 or Duncan disease, a rare immunodeficiency characterized by extreme susceptibility to infection with Epstein-Barr virus, with symptoms including severe mononucleosis and malignant lymphoma | Xq25-q26 | 0.8 |
| BCORL1 | BCL6 co-repressor-like 1 | unknown | Xq25-q26.1 | 1.3 |
| FHL1 | four and a half LIM domains 1 | LIM proteins, named for 'LIN11, ISL1, and MEC3,' are defined by the possession of a highly conserved double zinc finger motif called the LIM domain | Xq26 | 0.5 |
| CT45-4* | cancer/testis antigen CT45-4 | unknown | Xq26.3 | 0.8 |
| LOC644538* | hypothetical protein LOC644538 | unknown | Xq26.3 | 0.8 |
| RP13-36C9.1* | cancer/testis antigen CT45 | unknown | Xq26.3 | 0.7 |
| RP13-36C9.6* | cancer/testis antigen CT45-5 | unknown | Xq26.3 | 0.8 |
| LDOC1 | leucine zipper, down-regulated in cancer 1 | may regulate the transcriptional response mediated by the nuclear factor kappa B (NF-kappaB) | Xq27 | 0.6 |
| SLC6A8 | solute carrier family 6 (neurotransmitter transporter, creatine), member 8 | transports creatine into and out of cells; defects in this gene can result in X-linked creatine deficiency syndrome | Xq28 | 0.6 |

Figure 6:
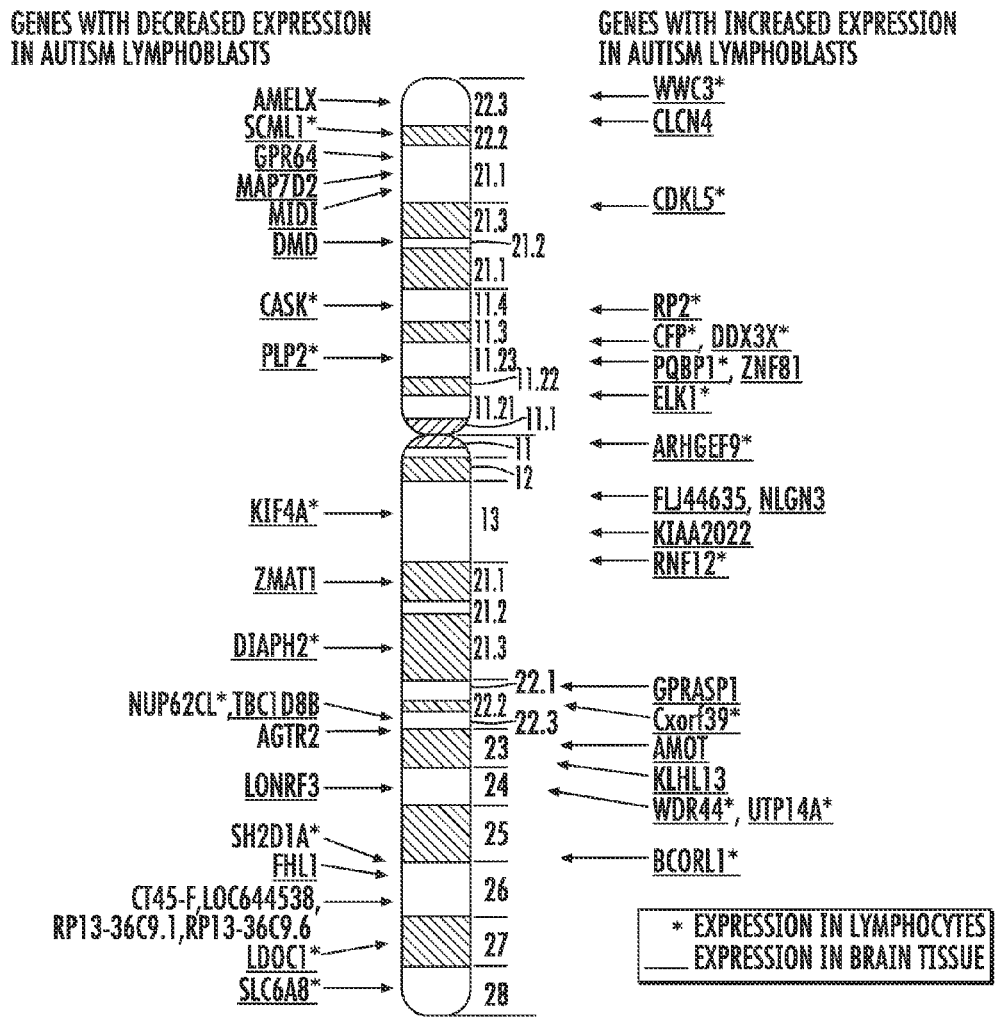
FIG. 6 represents an ideogram of the X chromosome showing the location of 44 genes that have been found to be expressed to a significantly different degree in individuals diagnosed with ASD. Genes expressed in the brain are shown underlined and genes expressed in lymphocytes are marked with an asterisk.

Of these 44 genes, 21 have been found to be up-regulated in affected individuals, with expression increases ranging from about 1.2 to about 2.7 fold, and 23 were found to be down-regulated in affected individuals, with expression decreases ranging from about 20% to about 70%. FIG. 6 is an ideogram representation of the X chromosome location of these 44 genes and illustrates either increased or decreased expression for each gene in individuals diagnosed with ASD. Accordingly, in one embodiment, probes for markers of these 44 genes can be utilized in forming a device, e.g., a microarray, for determining the expression level of these 44 genes in a test subject. Comparison of the expression levels of these genes with normal expression levels can provide information with regard to the predisposition of the tested individual for ASD. For example, statistically significant differences in expression levels for three or more of these 44 genes can signify an increased likelihood of the test subject having a predisposition for or being affected with ASD.

A set of markers for use as described herein is not limited to materials for expression detection of all of the 87 genes of Table 1 or all of the 44 genes of Table 2, however, and larger or smaller gene sets of the X-chromosome can be examined. For example, in order to obtain a smaller set of genes for use in determining predisposition toward or diagnosis of ASD, the 44 genes of FIG. 6 were further examined. Upon examination, it was determined that the differently expressed genes tend to cluster in several chromosomal locations including Xp11.2 to Xp11.4, Xp21 to Xp22, Xq23 to Xq 24 and Xq25. Accordingly, in one embodiment, disclosed methods and products are directed to determination of expression levels of genes found in one or more of these locations, and markers can encompass all or a portion of the genes within that area.

The 5 genes of Table 2 having the highest expression level and the 5 genes having the lowest expression level are DMD, CDKL5, MAP7D2, GPR64, SCML1, CLCN4, WWC3, KIAA2022, AMOT, FHL1. According to one embodiment, this set of 10 genes can be utilized in forming a device for detection of ASD or ASD predisposition.

As described further in the Examples section, below, eight of the above-listed 44 genes exhibited significantly altered expression in the greatest number of autism cases tested. Accordingly, in one embodiment, a set of markers for use as described herein can include markers for these eight genes, i.e., CLCN4, WDR44, NLGN3, CDKL5, KIAA2022, AMOT, MAP7D2, and TBC1D8B.

It has also been noted that the 44 genes of Table 2 are enriched with 11 genes known to play a role in metabolism and transcription. The 11 genes known to play a role in metabolism and transcription are CASK, CFP, CDKL5, LONRF3, RNF12, MID1, RP2, SCML1, ZNF81, ELK1, and PQBP1. Accordingly, this finding suggests that metabolism and transcription play a role in autism, and also suggests another subset of biomarkers for use in disclosed methods and devices. Specifically, metabolism and transcription genes on the X chromosome can be examined for altered expression level in a test subject according to disclosed methods, and in one embodiment, these particular 11 genes can be examined for expression levels.

Other subsets of the 44 genes of those provided in Table 2 can be utilized as disclosed herein. For instance, any group of three or more of the genes of Table 2 can be utilized as disclosed herein to determine a predisposition of an individual toward ASD.

Biomarkers as disclosed herein can be examined based upon the absolute expression level of the genes, the normalized expression levels of genes, or the relative expression levels of genes. Expression levels can be normalized by correcting the absolute expression level of a gene obtained from a test subject by comparing that expression to the expression of the same gene that is obtained from an individual not affected with ASD. Normalization can allow comparison of the expression level in one individual with that of another individual, for instance a family member of the tested subject.

In another embodiment, an expression level can be provided as a relative expression level. To determine a relative expression level of a gene, the level of expression of the gene can be determined for several individuals, e.g., at least two or more individuals, prior to the determination of the expression level for the sample in question, i.e., that of the test subject. The mean expression level of the examined genes assayed in the larger number of samples can be determined and used as a baseline expression level for the gene(s) in question. The expression level of the gene determined for the test sample (absolute level of expression) can then be divided by the mean expression value obtained for that gene. This can be provided as a relative expression level.

Biomarkers for determining activity of disclosed genes can generally be nucleotide sequences or proteins. In one embodiment, biomarkers for determining activity of disclosed genes can be nucleic acid sequences. Nucleic acid sequence biomarkers can include DNA molecules (e.g., cDNA or genomic DNA) and RNA molecules (e.g., mRNA). Nucleic acid biomarkers can optionally be analogs of DNA and RNA sequences as may be generated according to known methods as well as DNA and RNA sequences as may be utilized as hybridization probes to expression products of genes as disclosed herein.

Probes as may be utilized in disclosed devices can be a portion of a larger protein or nucleotide sequence. For instance, a probe can be an oligonucleotide or peptide sequence that can bind at 60° C. for about 17 hours to a marker as described herein (e.g., mRNA, cDNA, etc.). For example, an oligonucleotide probe can hybridize to between about 10 and about 60 consecutive nucleotides of a marker.

According to one embodiment, high to moderately stringent conditions, e.g., hybridization conditions, can be used to detect expression levels of disclosed genes.

Generally, highly stringent and wash conditions are selected to be about 5° C. lower than the thermal melting point ($T_m$) for the specific double-stranded sequence at a defined ionic strength and pH. For example, under "highly stringent conditions" or "highly stringent hybridization conditions" a nucleic acid will hybridize to its complement to a detectably greater degree than to other sequences (e.g., at least 2-fold over background). By controlling the stringency of the hybridization and/or washing conditions, nucleic acids that are 100% complementary can be identified.

The degree of complementarity or homology of hybrids obtained during hybridization is typically a function of post-hybridization washes, important factors being the ionic strength and temperature of the final wash solution. The type and length of hybridizing nucleic acids also affects whether hybridization will occur and whether any hybrids formed will be stable under a given set of hybridization and wash conditions. For DNA-DNA hybrids, the $T_m$ may be approximated from the equation of Meinkoth and Wahl (*Anal. Biochem.* 138:267 284 (1984)): $T_m=81.5°$ C.$+16.6$ (log M)$+0.41$ (% GC)$-0.61$ (% form)$-500/L$ where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. Very stringent conditions are selected to be equal to the $T_m$ for a particular probe.

An example of stringent hybridization conditions for hybridization of complementary nucleic acids that have more than 100 complementary residues on a filter in a Southern or Northern blot is 50% formamide with 1 mg of heparin at 42° C., with the hybridization being carried out overnight. An example of highly stringent conditions is 0.15 M NaCl at 72° C. for about 15 minutes. An example of stringent wash conditions is a 0.2×SSC wash at 65° C. for 15 minutes (see also, Sambrook, infra). Often, a high stringency wash is preceded by a low stringency wash to remove background probe signal. An example of medium stringency for a duplex of, e.g., more than 100 nucleotides, is 1×SSC at 45° C. for 15 minutes. An example of low stringency wash for a duplex of, e.g., more than 100 nucleotides, is 4× to 6×SSC at 40° C. for 15 minutes. For short probes (e.g., about 10 to 50 nucleotides), stringent conditions typically involve salt concentrations of less than about 1.0M Na ion, typically about 0.01 to 1.0 M Na ion concentration (or other salts) at pH 7.0 to 8.3, and the temperature is typically at least about 30° C.

The expression level of a gene can generally be detected through utilization of a detectable label. In general, any suitable detectable label can be utilized in detection of expression levels of disclosed genes. For example, a detectable label, e.g., a fluorescent label, a phosphorescent label, a radioisotope, and the like, can be bound to a molecule that can bind to biomarkers as described herein. In one embodiment, a detectable label can directly or indirectly specifically bind to a particular marker. For example, a detectably labeled oligonucleotide, polypeptide, or other organic compound can specifically bind to a biomarker as described herein so as to function as a probe for that biomarker. For example, a detectable probe can be a specific DNA or RNA sequence that can be hybridized to a marker and can be labeled for identification in solution.

In one preferred embodiment, an oligo microarray format can be utilized to determine the expression level of biomarkers. According to this embodiment, one or more specific probes for a biomarker can be anchored to a substrate surface such that biomarkers can bind, e.g., hybridize, to the probes for detection. Substrates can include, for example, microtitre plates of glass, quartz, silicon, polymeric substrates, and the like. Probes can include any oligonucleotide that can selectively hybridize to a nucleotide biomarker or any polypeptide that can selectively bind to a proteinaceous biomarker. An anchored probe can be any length as can effectively hybridize to a marker. For instance, an oligonucleotide probe can be about 60 nucleotides and can selectively hybridize to a marker at 60° C. for 17 hours. Oligonucleotide probes can be shorter or longer than 60 nucleotides. For example, an oligonucleotide probe can be about 20 nucleotides in length or longer, for instance about 30, about 40, or about 50 nucleotides in length.

A probe can be "fixed" to a substrate through either covalent or non-covalent association. In general, however, a probe can be bound to a substrate and washed to some significant degree of stringency. (e.g. standard saline citrate, pH 7.4) without a substantial fraction of the probe dissociating from the substrate. For example, probes can be printed onto a substrate using photolithography techniques using pre-made masks, dynamic micromirror devices, ink-jet printing, or electrochemical processes.

Optionally, a probe can be chemically bound to a substrate. For instance, a probe can be bound to a substrate via, for example, amine, carboxylic acid, hydroxy, aldehyde, thiol, or ester functionality on a prepared surface. For example, a substrate surface may be aminated through contact with an amine-containing compound such as 3-aminopropyltriethoxy silane in order to increase the amine functionality of the surface and bind a probe to the surface via the added amine functionality. A probe may be bound to a substrate via a streptavidin/biotin binding system, an antibody/hapten bridging system, and the like. It should be understood, however, that the binding of a probe to a substrate is not a requirement of disclosed systems, and in other systems, a probe can be in solution such that a marker/probe complex can be formed in solution.

According to one embodiment, RNA or proteinaceous biomarkers isolated from a cell culture, e.g., a lymphoblast cell culture, can be used to measure expression of targeted genes. In another embodiment, biomarkers can be extracted from peripheral lymphocytes of a test subject and quantified to determine the expression levels of the targeted genes. For example, transcribed RNA can be extracted from a sample through lysing of the cells and isolation of transcribed RNA into a suitable solution e.g., a buffered saline solution PBS according to standard methods as are generally known in the art. In general, the transcribed RNA can be converted to cDNA and amplified according to standard practices prior to quantification. For example, a standard cDNA synthesis kit amplification kit, such as that available from the Agilent Corporation, GE Healthcare, Sigma-Aldrich, and the like can be utilized.

The solution containing RNA biomarkers can be hybridized against a microarray containing probes for the markers. Upon contact between the solution comprising the genetic material and the probes, a probe/marker complex can form, for instance through hybridization of a marker with a probe. The complex can be detectably labeled either through labeling of a member of the complex prior to formation of the complex, at the same time as formation of the complex, or following formation of the complex. The quantity of marker can then be determined according to the signal strength of the detectable label, i.e., the signal strength of the detectable label can be proportional to the amount of the marker of the targeted gene. Expression levels of the targeted genes can be obtained through quantification of the microarray results using, e.g., a standardization or calibration signal obtained through use of a reference gene or the like, as discussed above.

In one embodiment, a microarray for determining expression level can include probes for all genes of the X chromosome. In another embodiment, a microarray can include probes for all 87 genes of Table 1 or all 44 genes of Table 2. In other embodiments, however, a microarray can be designed to examine a portion of a larger signature group, as previously discussed.

The above described expression microarray method is merely exemplary, however, and any method for detecting altered expression of brain expressed genes may be used to diagnose autism spectrum disorder, including, but not limited to real-time PCR, Northern blot analysis, and Luminex based assays. For example, overexpression or underexpression of a particular gene can be measured by comparing the amount (e.g., concentration) of the RNA product produced by the gene in a patient sample to the amount of RNA product produced by a non-affected person(s). If the person is determined to have an increased or decreased amount of RNA product compared to that of non-affected persons, then the person can be predisposed to autism. In one embodiment, an increased or decreased amount of about 20% or more of the RNA product signifies that the person is predisposed to autism.

In still another embodiment, the disclosure is directed to detecting an increase or decrease in a protein expression product of a brain expressed gene(s) in an individual, in order to determine that individual's predisposition to autism spectrum disorder. Any method of detecting the amount of expression of the protein products of brain expressed genes may be utilized to diagnose autism spectrum disorder, including, but not limited to, Western blot analysis, protein sequencing, 2-D gel electrophoresis, mass spectrometry, protein microarrays, assays measuring enzyme activity, methods to determine altered protein-protein interactions, and assays to detect protein modifications.

For example, a protein microarray similar to the genetic microarrays previously described including probes for markers of the protein products of disclosed genes can be utilized to determine predisposition of an individual for ASD. For instance, complete antibodies can be bound to a microarray surface or optionally fragments thereof that can be used to bind the targeted biomarker. Probes can be natural or synthetic agents. For example, a peptide as can be formed using any variation of phage display protocol or the like, can be used as a probe. In another embodiment, probes can include (Fab)' fragments of the corresponding antibody. An Affibody® can also be utilized. Affibody® affinity ligands are research reagents available from Abcam. They are small, simple proteins composed of a three-helix bundle based on the scaffold of one of the IgG-binding domains of Protein A, a surface protein from the bacterium *Staphylococcus aureus*. The scaffold has features as an affinity ligand and can be designed to bind with high affinity to any given target proteinaceous biomarker.

Antibodies to the targeted biomarkers as can be utilized as probes can include polyclonal or monoclonal antibodies as desired. Antibodies can be raised according to known methods. For instance, one or more isolated and/or purified or recombinantly produced biomarker proteins may be utilized to generate the antibodies using the methods known in the art.

An increase or decrease in concentration or activity of protein expression product for three or more protein products of disclosed genes in a patient sample, compared to that of a non-affected person(s), can signify that the person may be predisposed to autism. In one embodiment, an increased or decreased concentration or activity of about 20% or more of the protein expression product signifies that the person is predisposed to autism.

Disclosed herein is the discovery that alterations in methylation, which can cause one or more genes on the single X chromosome in males to be partially or totally silenced or overexpressed, can constitute a predisposition to autism spectrum disorders. The marked excess of males among individuals with autism, the preponderance of sporadic cases of autism, and the absence of malformations and dysmorphism that often accompany gene mutations that completely extinguish gene expression are consistent with this epigenetic cause of autism.

Even though females are less frequently affected with autism, the hypomethylation or hypermethylation of brain expressed genes on the X chromosome is equally applicable as a potential explanation for autism in females. Here, one or more gene loci on the active X chromosome in females is believed to be partially silenced or over-expressed. Two factors, however, can moderate the autism predisposition, decreasing the prevalence of autism in females. First is the presence of a second X chromosome which may compensate for dysregulated methylation on the other X chromosome. Second is skewing of X-inactivation through which the more normally functioning X chromosome has an advantage and is used preferentially.

Partial silencing or overexpression of the brain expressed genes on the single X chromosome in males (or on the single active X chromosome in females) has not previously been identified as a biological phenomenon of significance in autism spectrum disorders. Yet, such a hypohaploid state might plausibly occur if the male's single X chromosome inherited from his mother was excessively methylated. Such incomplete erasure of methylation might occur in situations where the demethylating capacity was lowered for whatever reason (dietary, metabolic, genetic). Conversely, a hyperhaploid expression profile might plausibly occur if the X chromosome in males is hypomethylated in comparison to control samples.

Reference now will be made to the embodiments of the disclosure, examples of which are set forth below. Each example is provided by way of an explanation of the disclosure, not as a limitation of the disclosure. In fact, it will be apparent to those skilled in the art that various modifications and variations can be made in the disclosure without departing from the scope or spirit of the disclosure. For instance, features illustrated or described as one embodiment can be used on another embodiment to yield still a further embodiment.

Example 1

DNA isolated from peripheral lymphocytes from 5 normal males and 5 males with autism was treated with RNase for 3 hr and then sonicated to an average length of 300-500 bp. After extraction with phenol/chloroform and ethanol precipitation, pellets were resuspended and the resulting DNA was quantified on a Nanodrop spectrophotometer. DNA (3-15 μg) was precleared with protein G agarose beads (Invitrogen). Methylated DNA was detected using a sheep polyclonal antibody against 5-methyl-cytosine. After incubation at 4° C. overnight, protein G agarose beads were used to isolate the immune complexes. Complexes were washed and eluted from the beads with SDS buffer. Immunoprecipitated (IP) DNA was purified by phenol/chloroform extraction and ethanol precipitation. Quantitative PCR (qPCR) reactions were carried out in triplicate on specific genomic regions using SYBR Green Supermix (Bio-Rad). The resulting signals were normalized for primer efficiency by carrying out QPCR for each primer pair using input (unprecipitated) DNA. IP and input DNAs were amplified by Whole Genome Amplification (WGA) using the GenomePlex WGA kit (Sigma). The resulting amplified DNA was purified, quantified, and tested by qPCR at the same genomic regions as the original immunoprecipitated DNA to assess quality of the amplification reactions. Amplified DNAs were sent to NimbleGen for custom X chromosome methylation microarray analysis.

IP and input samples were labeled in separate reactions with Cy5 and Cy3, respectively.

Labeled IP and input samples were pooled, denatured, and subsequently co-hybridized to a custom NimbleGen X Chromosome DNA Methylation array (2007-06-05_HG18_JJ_METH).

Data was extracted using NimbleScan software, the ratio of IP versus input was calculated, peaks (methylated regions) were called and then mapped to the transcription start site of a gene. DNA methylation data were visualized with SignalMap software. From the raw data, NimbleScan software generated scaled log 2-ratio data for IP/input values and p-value enrichment data for each probe using a statistical method. Peaks (methylated regions) were then generated based on the p-value data. These data were visualized along in the SignalMap data browser (FIG. 1). Three of the five autism samples showed a significant reduction in global DNA methylation along the entire length of the X chromosome compared to normal male controls.

Example 2

DNA isolated from peripheral lymphocytes from 44 normal males and 41 males with autism was digested with the methylation-sensitive restriction enzyme Hpall. Real-time PCR was performed on digested genomic DNA using the ABI Prism® 7000 sequence detection system (Applied Biosystems, Foster City, Calif.). In order to ensure the DNA was completely digested, PCR was performed using primers that flank a Hpall site in the first exon of the androgen receptor gene expected to be completely unmethylated in a male with a single X chromosome (Allen et al. 1992). The Primer Express® computer software was used to design primers that flank one Hpall site within exon 1 and flanking sequence of the candidate X-linked genes. SYBR® Green chemistry (Applied Biosystems, Foster City, Calif.) was used in the amplification of target genes. RNaseP was used as an endogenous control, and the RNaseP probe/primer mix which uses TaqMan® chemistry was obtained commercially as a kit from Applied Biosystems. Optimal primer concentrations were determined as previously described (Livak and Schmittgen 2001). The comparative Ct method was used for relative quantification of methylation. The amount of target relative to a calibrator (undigested DNA from a normal male), both normalized by an endogenous control (RNaseP), was calculated from the following formula:

relative methylation=$2^{-\Delta\Delta Ct}$ where: $\Delta Ct = Ct(\text{target}) - Ct(\text{RNaseP})$ $\Delta\Delta Ct = \Delta Ct(\text{sample}) - \Delta Ct(\text{calibrator})$ For each gene analyzed, the calculated methylation value of the calibrator (undigested DNA from a normal male) was set to 1.0, and the calculated methylation values for the samples were then expressed relative to the calibrator. This value reflects the percent of cells methylated at the selected CpG site. The calculated methylation values for the autism cohort were compared to the calculated values for the normal controls.

Figure 3:
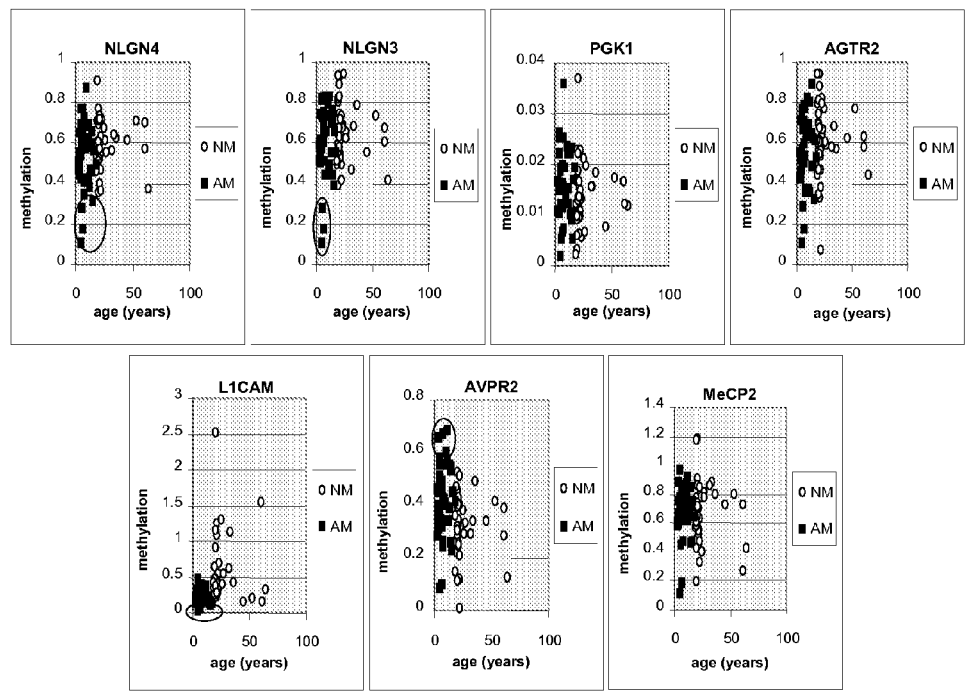
FIG. 3 represents scatterplots of the degree of methylation of selected genes on the X chromosome in males with autism (solid squares) and unaffected males (open circles). The squares encircled on the scatterplots for NLGN4, NLGN3, L1CAM, and AVPR2 identify males with autism whose methylation values fall outside the range of values for unaffected males.

To test the difference between the methylation values for the digested male autism patients and digested male controls, the conservative Wilcoxon's rank-sum test was used (data not shown). The results from this test were similar to results from the Student's t-test; however, the t-test assumption of normality (using the Shapiro-Wilk normality test) was not satisfied for data from four of the seven genes studied. These statistical tests were run using the statistical programming language R (The R Foundation for Statistical Computing 2004). No significant difference in overall methylation status was observed between patients and controls for the PGK1, MECP2, NLGN4, NLGN3, and AGTR2 genes, although decreased methylation of NLGN4 and NLGN3 was observed in some autism patients (n=4 and 3, respectively) (FIG. 3). Autistic males had a statistically significant decrease ($P \leq 0.01$) in L1CAM methylation as compared to controls. The autistic males were hypermethylated at a CpG within the promoter region of AVPR2, the gene adjacent to L1CAM, when compared to the control group ($P \leq 0.01$).

Example 3

One autism case whose methylation value for L1CAM was clearly lower than the methylation values of the 44 controls was used to determine whether methylation correlates with gene expression. Native RNA from the case, his mother, and identical twin with autism were utilized in this study. Total RNA was isolated from peripheral blood samples collected in PAXgene™ blood RNA tubes (PreAnalytiX GmbH, Hombrechtikon, Switzerland) using the Versagene™ RNA blood kit. cDNA was generated using the SuperScript™ III First-Strand Synthesis System for RT-PCR (Invitrogen Life Technologies, Carlsbad, Calif.). Gene expression was determined by real-time PCR using TaqMan® Assays-on-Demand™ Gene Expression products and the ABI PRISM® 7000 Detection System (PE Biosystems, Foster City, Calif.). All quantitations were normalized to GAPDH RNA and expressed as fold changes relative to a normal male control using the comparative Ct method.

Figure 4:
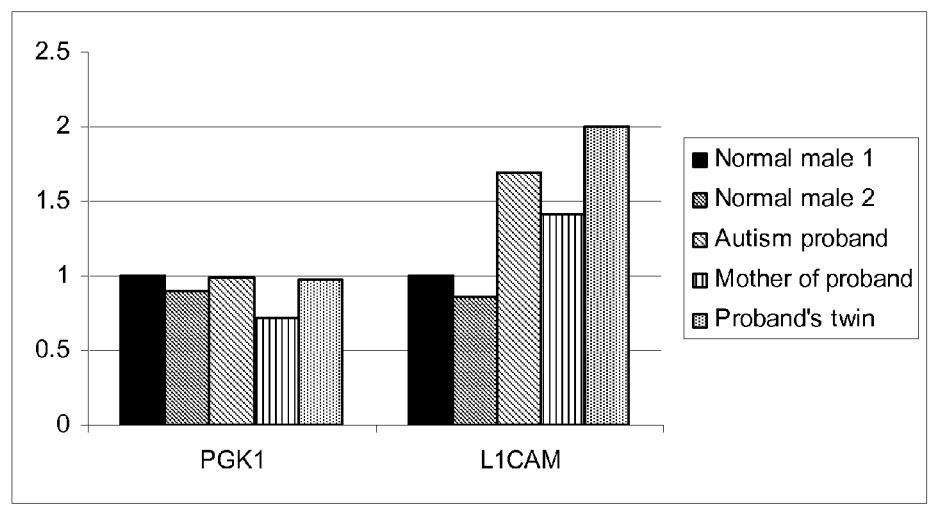
FIG. 4 represents an expression of L1CAM as determined by real-time PCR in a male with autism, his mother, his affected identical twin brother, and two unaffected (normal) males. The overexpression of L1CAM alone or in combination with overexpression or underexpression of other brain expressed genes on the X chromosome can predispose for autism.

Expression of L1CAM was measured in these three individuals and compared to expression in two control male RNA samples (FIG. 4). The autism case, his autism-affected brother, and the mother had overexpression of the L1CAM gene in comparison to the two control males. The relative increases were 1.7-fold (proband), 1.4-fold (mother) and 2.0-fold (twin with autism). Similar results were found on repeat of the expression analysis. Because of the magnitude of the increased expression, the copy number of the L1CAM gene was verified using multiplex ligation-dependent probe amplification (MLPA). Only a single copy of the L1CAM gene was found in the autism male and his identical twin.

Example 4

Figure 5:
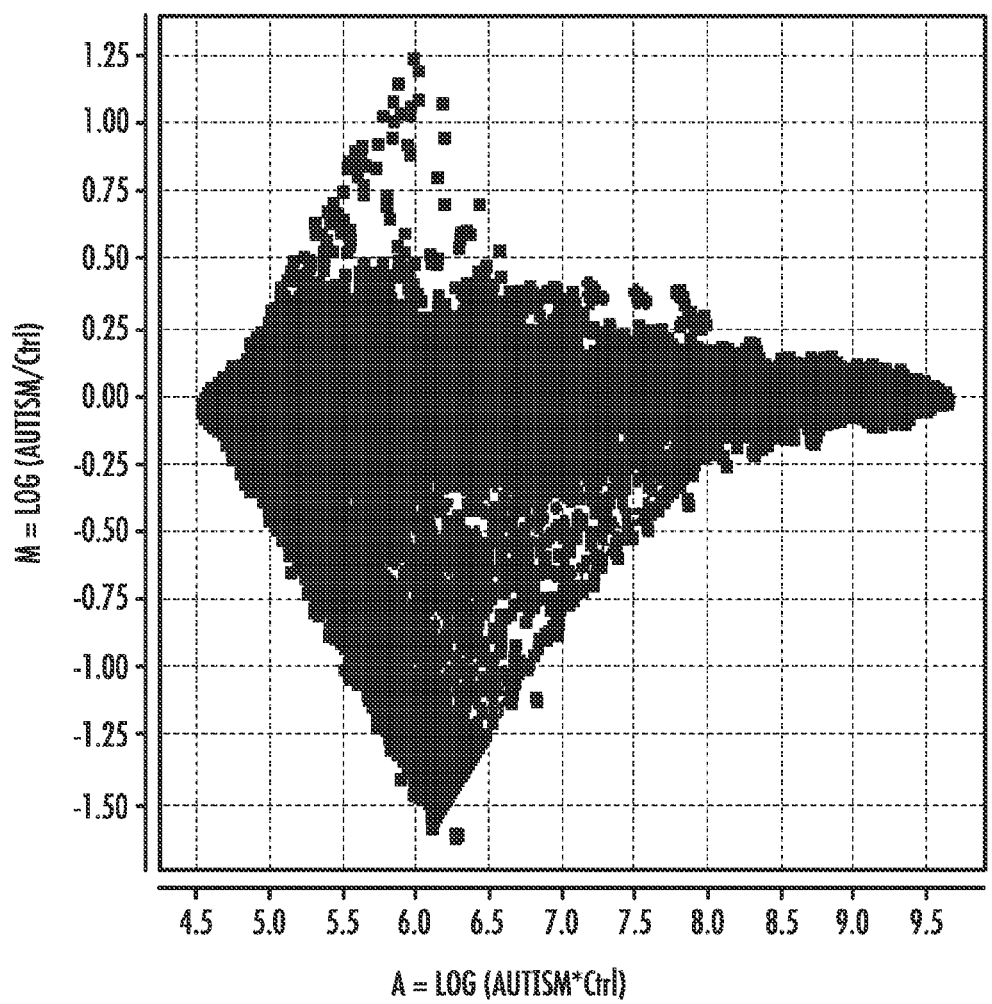
FIG. 5 represents an MA plot for X-chromosome sample non-redundant probes. Each dot represents the log [ratio of probe intensity of the averaged autism (17 samples) vs. control (10 samples)] plotted against the log [probe intensity of the averaged autism (17 samples)×control (10 samples)]; M: Log(Autism intensity/Control intensity); A: Log(Autism intensity×Control intensity).

An analysis was conducted of expression of X chromosome genes using a NimbleGen custom X chromosome gene expression array (HG18_JJ_60mer_EXPR) on 10 age matched normal (control) and 17 well characterized autistic patients. The array is comprised of 25,668 probes with seven replicates of each probe. Multiple copies of probes represent each unique DNA sequence. It was reasoned that each probe, in fact, represents a technical replicate of a unique segment of the gene. Thus, all of the replicated probes were combined under the same accession number. This resulted in a list of 2,965 nonredundant 'meta-probes'. The distribution of individual 'meta-probes' was inspected using an MA plot and found them to have a good distribution (see FIG. 5), and no further normalization was required. These 2,965 transcripts correspond to 784 unique genes on the X chromosome. With the exception of a few genes having highly repetitive sequences making probe design too difficult, these 784 genes represent all genes noted to be located on the human X chromosome when the array was designed.

The fold change for gene expression was calculated as the ratio of fluorescence intensity of the autism group divided by control cohort. The fold changes were then transformed into logarithmic scale. To select the genes that were differentially expressed in microarray experiments, a statistical program was utilized: Significance Analysis of Microarray (SAM) (Tusher V G, Tibshirano R, Chu G: Significance analysis of microarrays applied to the ionizing radiation response. Proc Natl Acad Sci USA 98:10515, 2001), which implements a modified t-test based on the false discovery rate (FDR) (Pounds and Morris 2003, Reiner et al. 2003, Storey and Tibshirani 2003, incorporated herein by reference). The threshold for the false discovery rate was set at 0.10, i.e., an estimated 10% of the genes called significant could be false.

Using an FDR at 0.1, forty-four (44) genes were identified having expression qualified as significantly different between the autism and control cohorts (Table 2, above). Four features are worth noting: 1) the genes tend to cluster in several chromosomal locations. For example, Xp11.2-Xp11.4, Xp21-Xp22, Xq23-24, and Xq25; 2) multiple genes are known to be involved in human diseases, including CDKL5 (atypical variant of Rett syndrome), MID1 (Opitz/BBB syndrome), and DMD (Duchenne and Becker Muscular Dystrophies); 3) one gene, NLGN3, is directly related to autism; and 4) as a group the gene list suggests that metabolism and transcription play a role in autism, because the list is enriched with such genes (11 out of 44 genes), including CASK, CFP, CDKL5, RNF12, MID1, PQBP1, SCML1, and ELK1 among others. With the exception of 7 genes (noted by asterisks in Table 2), the genes in Table 2 are all expressed in the human brain, although CFP, GPR64, and FLJ44635 are expressed at very low levels as is known in the art and further described at the NCBI website (www.ncbi.nlm.nih.gov/sites/entrez?db=unigene).

It is intuitive to verify genes that are altered in autism samples with greater magnitudes, for example the 5 with highest expression and the 5 genes with lowest expression as discussed above. This list contains genes previously known to cause diseases when mutated (such as CDKL5 and DMD) and genes involved in important cellular function including endothelial tube formation and migration (AMOT), and possibly signal transduction (WWC3, GPR64, and MAP7D2) and transcriptional regulation (FHL1).

Figure 7:
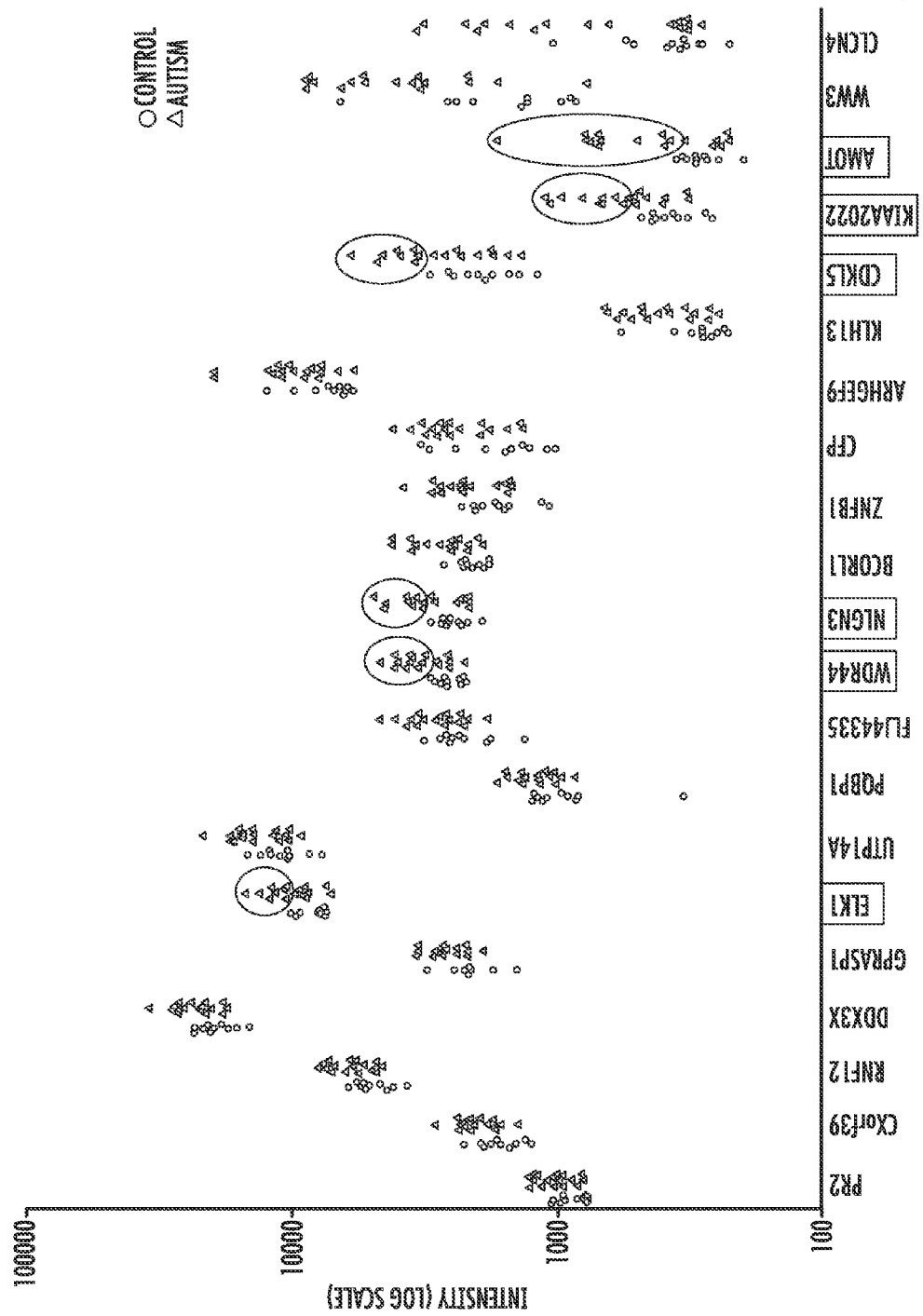
FIG. 7 represents scatterplots of the degree of expression of selected genes on the X chromosome that are generally overexpressed in males with autism (solid triangles) as compared to unaffected males (open circles). Each of the five genes with triangles encircled on the scatterplots have 8 or more autism samples with expression values above the range of values for unaffected males.

In the above analyses, gene expression was compared between the normal and autistic patients based on the groups' averaged values. Scatter plots were prepared to depict the distribution of the gene expression of the 44 X chromosome genes between the normal and autistic patients (FIGS. 7 (overexpression), and 8 (underexpression)). The results in the figures clearly demonstrate a trend of difference in expression of these X chromosome genes between the normal and the autistic patients. For instance, the circled results on FIGS. 7 and 8 indicate the genes with 8 or more of the 17 autism cases exhibiting altered expression.

Example 5

An algorithm to identify individuals predisposed to ASD based on the expression level of X-chromosome genes was carried out. Expression levels were determined using an expression microarray for X-chromosome genes. Eight X-chromosome genes were selected for this example: CLCN4, WDR44, NLGN3, CDKL5, KIAA2022, AMOT, MAP7D2, and TBC1D8B. Fifteen of 17 individuals with autism had expression levels outside (above or below) the control range for 3 or more of the 8 genes.

Thus, in this scenario using the criteria of expression of three or more genes outside the normal range, 15 of the 17 individuals with autism would have been identified. There were no false positives for a specificity of 100% and two false negatives for a sensitivity of 88.2%.

These and other modifications and variations to the present disclosure may be practiced by those of ordinary skill in the art, without departing from the spirit and scope of the present disclosure. In addition, it should be understood the aspects of the various embodiments may be interchanged, either in whole or in part. Furthermore, those of ordinary skill in the art will appreciate that the foregoing description is by way of example only, and is not intended to limit the disclosure.

What is claimed is:

1. A method for determining predisposition to or diagnosis of autism spectrum disorder in an individual, comprising:
    isolating DNA from cells of an individual;
    digesting the DNA;
    performing polymerase chain reaction using primers that flank a HpaII site in the first exon of and flanking sequence of each gene of a set of genes of the individual, wherein the set of genes comprises NLGN4, NLGN3, L1CAM, and AVPR2;
    determining the cytosine methylation level of the genes;
    comparing the cytosine methylation level of the genes to a control cytosine methylation level of corresponding genes; and
    finding that at least three of NLGN4, NLGN3, L1CAM and AVPR2 of the individual are hypermethylated or hypomethylated as compared to the control cytosine methylation level of the corresponding genes to determine that the individual is predisposed to or affected with autism spectrum disorder.

2. The method according to claim 1, wherein all of the genes of the set comprise XLMR genes.

3. The method according to claim 1, wherein the set of genes further comprises one or more of ARHGEF6, AGTR2, ALDP, AP1S2, ARHGEF9, ARX, ATP6A8-9, ATP7A, BCOR, BRWD3, CUL4B, DCX, DDP, DKC1, DLG3, DMD, FACL4, FANCB, FGD1, FLNA, FMR1, FMR2, FTSJ1, GDI1, GKD, GPC3, GRIA3, HADH2, HCCS, HPRT, HUWE1, IDS, IGBP1, IL1RAPL, JARID1C, KIAA1202, KIAA2022, KLF8, LAMP2, MAOA, MBTPS2, MECP2, MED12, MID1, MTM1, NDP, NDUFA1, NEMO, NHS, NXF5, OCRL1, OFD1, OPHN1, OTC, PAK3, PCDH19, PDHA1, PGK1, PHF6, PHF8, PLP, PORCN, PQBP1, PRPS1, RPL10, RSK2, SLC16A2, SLC6A8, SLC9A6, SMC1A/SMC1L1, SMS, SOX3, SRPX2, CDKL5, SYN1, TM4SF2, UBE2A, UPF3B, XNP, ZDHHC9, ZDHHC15, ZNF41, ZNF674, and ZNF81.

4. The method according to claim 1, wherein the set of genes further comprises one or more of STK9, ARX, AGTR2, FMR1, RPL10, SLC6A8, MECP2, ARHGEF6, FACL4, MED12, JARID1C, TM4SF2, and AP1S2.

5. The method according to claim 1, wherein the cytosine methylation level comprises the methylation level of cytosines at CpG dinucleotide sites.

6. The method according to claim 3, wherein the set of genes comprises at least 15 genes, the method further comprising finding that at least about 20% of the genes of the set are hypermethylated or hypomethylated as compared to the control cytosine methylation level of the corresponding genes.

7. The method according to claim 1, wherein the set of genes comprises STK9, ARX, AGTR2, FMR1, RPL10, SLC6A8, MECP2, ARHGEF6, FACL4, MED12, JARID1C, TM4SF2, and AP1S2, the method further comprising finding that at least about 20% of the genes of the set are hypermethylated or hypomethylated as compared to the control cytosine methylation level of the corresponding genes.

8. The method according to claim 1, wherein the cells are peripheral lymphocytes.

9. A method for determining predisposition to or diagnosis of autism spectrum disorder in an individual comprising:
    isolating DNA from cells of an individual;
    digesting the DNA;
    performing polymerase chain reaction using primers that flank a HpaII site in the first exon of and flanking sequence of each of at least fifteen brain expressed genes on the X chromosome of the individual, wherein the brain expressed genes on the X chromosome are selected from ARHGEF6, AGTR2, ALDP, AP1S2, ARHGEF9, ARX, ATP6A8-9, ATP7A, BCOR, BRWD3, CUL4B, DCX, DDP, DKC1, DLG3, DMD, FACL4, FANCB, FGD1, FLNA, FMR1, FMR2, FTSJ1, GDI1, GKD, GPC3, GRIA3, HADH2, HCCS, HPRT, HUWE1, IDS, IGBP1, IL1RAPL, JARID1C, KIAA1202, KIAA2022, KLF8, L1CAM, LAMP2, MAOA, MBTPS2, MECP2, MED12, MID1, MTM1, NDP, NDUFA1, NEMO, NHS, NLGN3, NLGN4, NXF5, OCRL1, OFD1, OPHN1, OTC, PAK3, PCDH19, PDHA1, PGK1, PHF6, PHF8, PLP, PORCN, PQBP1, PRPS1, RPL10, RSK2, SLC16A2, SLC6A8, SLC9A6, SMC1A/SMC1L1, SMS, SOX3, SRPX2, CDKL5, SYN1, TM4SF2, UBE2A, UPF3B, XNP, ZDHHC9, ZDHHC15, ZNF41, ZNF674, and ZNF81;
    determining the cytosine methylation level of the at least fifteen brain expressed genes;
    comparing the cytosine methylation level of the at least fifteen brain expressed genes to a control cytosine methylation level of corresponding genes; and
    finding that at least 20% of the brain expressed genes of the individual are hypermethylated or hypomethylated as compared to the control cytosine methylation level of the corresponding genes to determine that the individual is predisposed to or affected with autism spectrum disorder.

10. The method according to claim 9, wherein the control cytosine methylation level is developed from data obtained from a control group comprising non-affected age matched individuals.

11. The method according to claim 9, wherein the cytosine methylation level comprises the methylation level of cytosines at CpG dinucleotide sites.

12. The method according to claim 9, wherein the cells are peripheral lymphocytes.

* * * * *